(12) United States Patent
Lanier, Jr. et al.

(10) Patent No.: US 8,361,801 B2
(45) Date of Patent: Jan. 29, 2013

(54) DEVICES, SYSTEMS, AND METHODS FOR AIDING IN THE DETECTION OF A PHYSIOLOGICAL ABNORMALITY

(75) Inventors: Gregory R. Lanier, Jr., Manchester, NH (US); Derek G. Kane, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 112 days.

(21) Appl. No.: 12/423,352

(22) Filed: Apr. 14, 2009

(65) Prior Publication Data

US 2010/0041062 A1 Feb. 18, 2010

Related U.S. Application Data

(60) Provisional application No. 61/044,891, filed on Apr. 14, 2008.

(51) Int. Cl.
*G01N 33/00* (2006.01)
(52) U.S. Cl. ............................ 436/127; 436/63; 436/811
(58) Field of Classification Search .................. 436/127, 436/63, 811
See application file for complete search history.

(56) References Cited

U.S. PATENT DOCUMENTS

| | | | |
|---|---|---|---|
| 3,507,146 | A | 4/1970 | Campbell et al. |
| 5,285,794 | A | 2/1994 | Lynch |
| 5,705,735 | A | 1/1998 | Acorn |
| 5,960,792 | A | 10/1999 | Llyod et al. |
| 2001/0050080 | A1 | 12/2001 | Seakins et al. |
| 2002/0029003 | A1 | 3/2002 | Mace et al. |
| 2002/0173728 | A1 | 11/2002 | Mault |
| 2003/0105407 | A1 | 6/2003 | Pearce, Jr. et al. |
| 2004/0186389 | A1 | 9/2004 | Mault et al. |
| 2004/0186390 | A1 | 9/2004 | Ross et al. |
| 2004/0254501 | A1 | 12/2004 | Mault |
| 2005/0065448 | A1 | 3/2005 | Stahmann et al. |
| 2005/0197589 | A1 | 9/2005 | Kline |
| 2007/0062536 | A1* | 3/2007 | McAuley et al. ........ 128/206.21 |
| 2007/0078357 | A1 | 4/2007 | Kline |

FOREIGN PATENT DOCUMENTS

GB 2146781 A 4/1985

OTHER PUBLICATIONS

Clinical Trials, "Breath Analysis Technique to Diagnose Pulmonary Embolism", Aug. 24, 2006.*
Impact of anaesthesia-surgery on D-dimer concentration and end-tidal CO2 and O2 in patients undergoing surgery associated with high risk of pulmonary embolism, Kline et al., Clinical Psychology and Functional Imagining, col. 28, Issue 3, pp. 161-168 (Feb. 12, 2008).

* cited by examiner

*Primary Examiner* — Jill Warden
*Assistant Examiner* — Monique Cole
(74) *Attorney, Agent, or Firm* — Pierce Atwood LLP; Kevin M. Farrell; David J. Wilson

(57) ABSTRACT

The present invention comprises a method for identifying the presence or absence of a pulmonary embolism using a combination of tests and brightline thresholds. The first test is a blood based test measuring D-Dimer concentration and the second test is a respiratory analysis that determines a carboximetry ratio. If the measured D-Dimer value is at or above a threshold indicative of concern and the carboximetry value is equal to or less than a carboximetry ratio threshold, pulmonary embolism is present. If the measured D-Dimer value is at or above a threshold indicative of concern and the respiratory analysis yields a carboximetry ratio greater than the carboximetry ratio threshold, test results are inconclusive and additional testing is required to determine whether a pulmonary embolism is present.

12 Claims, 31 Drawing Sheets

DEVICES, SYSTEMS, AND METHODS FOR AIDING IN THE DETECTION OF A PHYSIOLOGICAL ABNORMALITY

RELATED APPLICATIONS

The present application claims priority to U.S. Provisional Application No. 61/044,891 filed on Apr. 14, 2008, the entire content of which is incorporated by reference.

BACKGROUND OF THE INVENTION

1. Field of the Invention

The present invention relates generally to the field of medical devices and diagnostics, and more specifically to the field of non-invasive devices, systems and methods for aiding in the detection of a physiological abnormality identifiable through analysis of contents of a quantity of breathed air.

2. History of the Related Art

Contents and airflow characteristics of breathed air vary with physical condition. Different physical abnormalities manifest certain detectable and measurable variations in those contents. One example of a physiological abnormality identifiable through analysis of measured contents and flow characteristics of a quantity of breathed air is a pulmonary embolism. A pulmonary embolism occurs when an embolus becomes lodged in a lung artery, thus blocking blood flow to lung tissue. An embolus is usually a blood clot, known as a thrombus, but may also comprise fat, amniotic fluid, bone marrow, tumor fragments, or even air bubbles that block a blood vessel. Unless treated promptly, a pulmonary embolism may be fatal.

Like many physiological abnormalities, a pulmonary embolism may be difficult to detect because signs and symptoms may vary depending on the severity of the occurrence. For instance, a pulmonary embolism may be confused with a heart attack, pneumonia, hyperventilation, congestive heart failure or a panic attack. In other cases, no symptoms manifest at all.

A physician will sometimes first eliminate the occurrence of other diseases or dysfunctions before determining a true cause of the physiological abnormality. In the example of a pulmonary embolism, traditional diagnostic methods of testing involve blood tests, chest X-rays, and electrocardiograms. These methods typically may be more effective in ruling out other possible problems than in actually diagnosing a pulmonary embolism. For example, a chest x-ray may reveal subtle changes in the blood vessel patterns after an embolism and signs of pulmonary infarction. However, chest x-rays may show normal lungs even when an embolism is present. Similarly, an electrocardiogram may show abnormalities that are useful mainly in establishing the possibility of a pulmonary embolism.

As a pulmonary embolism alters the ability of the lungs to oxygenate the blood and to remove carbon dioxide from the blood, one method of diagnosing the condition involves taking a specimen of arterial blood and measuring the partial pressure of oxygen and carbon dioxide in the arterial blood (i.e., an arterial blood gas analysis). Although a pulmonary embolism often causes abnormalities in these measurements, an individual finding or combination of findings from the arterial blood gas analysis does not necessarily provide a reliable way to exclude or a specific way of diagnosing a pulmonary embolism. For instance, some patients with a documented pulmonary embolism have normal oxygen and carbon dioxide contents of the arterial blood. Accordingly, the arterial blood analysis may not reliably include or exclude the diagnosis of a pulmonary embolism.

The blood D-dimer assay is another diagnostic method that has become available for commercial use. A D-dimer protein fragment is typically formed when fibrin is cleaved by plasmin and therefore produced naturally whenever clots form in the body. However, many studies have shown a D-dimer assay may produce a high degree of false positives when evaluating a patient for pulmonary embolism.

In an attempt to increase the accuracy of diagnostic procedures for pulmonary embolisms, physicians have recently turned to methods that can produce an image of a potentially afflicted lung. One such method is a nuclear perfusion study that involves the injection of a small amount of radioactive particles into a vein. The radioactive particles then travel to the lungs where they highlight the perfusion of blood in the lung based upon whether they can penetrate a given area of the lung. One possible drawback to this method, however, is that an abnormal scan does not necessarily mean that a pulmonary embolism is present.

Pulmonary angiograms are another means of diagnosing a pulmonary embolism. During a pulmonary angiogram, a catheter is threaded into the pulmonary artery so that iodine dye can be injected into the bloodstream. The dye flows into the regions of the lung, defining the lung's arteries in an x-ray image. This technique may indicate a pulmonary embolism as a blockage of flow in an artery. Although a pulmonary angiogram may be useful in diagnosing a pulmonary embolism, this technique often presents health risks in addition to imposing a burdensome cost.

Spiral volumetric computed tomography is another diagnostic tool that has been proposed recently as a possibly less invasive test for detecting a pulmonary embolism. This procedure's reported sensitivity has varied widely; Spiral volumetric tomography may provide utility only for diagnosing an embolism in the central pulmonary arteries because of a relatively insensitivity to clot detection in more remote regions of the lungs.

The pulmonary vascular imaging tests described above have several disadvantages in common. Many of the tests require ionizing radiation and invasiveness of, at a minimum, an intravenous catheter. Some tests also typically involve costs of more than $1,000 for the patient, take more than two hours to perform, and require special expertise such as a trained technician to perform the tests and acquire the images and a board-certified radiologist to interpret the images. Notably, many of the tests may be questionably safe for patients who are pregnant. As a result of these shortcomings, many of the imaging procedures currently in use are unavailable in many outpatient clinic settings. Accordingly, there is a need in the art for a system, device and method that are readily usable in an outpatient setting for aiding in the diagnosis of physiological abnormalities including, for example, pulmonary embolisms, whose symptoms manifest in detectable, measurable variations in the contents and characteristics of breathed air.

SUMMARY OF THE INVENTION

One embodiment of the invention is a method for identifying the presence or potential presence of a pulmonary embolism using a combination of tests and thresholds. The method first comprises measuring a D-dimer concentration in a blood sample and determining whether the D-dimer concentration falls at or above a threshold beneath which pulmonary embolism is excluded, thereby producing a positive D-dimer test result for pulmonary embolism. If the D-Dimer threshold falls below a threshold indicative of concern, the method comprises indicating that no pulmonary embolism exists and that no further testing for pulmonary embolism is required. If the D-Dimer concentration falls at or above the threshold, the method next comprises measuring a concentration of produced carbon dioxide in a volume of exhaled air and measuring a concentration of unconsumed oxygen in the volume of exhaled air. After these concentrations are measured, the method comprises calculating a carbox ratio wherein the carbox ratio represents the concentration of produced carbon dioxide in relation to the concentration of unconsumed oxygen. The method next comprises comparing the calculated carbox ratio to a known carbox value indicating the presence of a pulmonary embolism to determine whether a pulmonary embolism exists. In one embodiment, the known carbox value that indicates the presence of a pulmonary embolism falls within a range of 0.25 to 0.30 and more preferably is 0.28. The method further comprises either outputting an indication that a pulmonary embolism exists, or, in cases when the calculated carbox ratio is above the carbox ratio threshold, outputting an indication that additional diagnostic testing is required.

Another embodiment of the invention is an improved method for identifying pulmonary embolism in patients. The method comprises determining whether a concentration of D-dimer in a blood sample is at or above a threshold indicative of concern. The method comprises determining, in cases when the D-dimer concentration is at or above the threshold indicative of concern, a carbox ratio of a volume of exhaled air; and outputting an indication, in cases when the carbox ratio is less than or equal to a carbox ratio threshold, that a pulmonary embolism is likely.

Yet another embodiment of the invention is an improved method for identifying pulmonary embolism in patients. The method comprises determining whether a concentration of D-dimer in a blood sample is at or above a threshold indicative of concern. The method comprises determining whether a carbox ratio of a volume of exhaled air is less than or equal to a carbox ratio threshold, and outputting an indication, in cases when the concentration of D-dimer in the blood sample is at or above a threshold indicative of concern and the carbox ratio is less than or equal to the carbox ratio threshold, that a pulmonary embolism is likely.

The present invention is described below in detail according to its preferred embodiments with reference to the following figures.

DETAILED DESCRIPTION OF THE PREFERRED EMBODIMENTS

The present invention includes a system, a device, and a removable mouthpiece for aiding in the diagnosis of a physiological abnormality resulting variations of detectable and measurable contents and characteristics of breathed air. Various features and advantages of the present invention are described below with reference to several preferred embodiments and variations thereof. However, it should be understood by those skilled in the art that the scope of the present invention is defined by the appended claims.

Figure 1A:
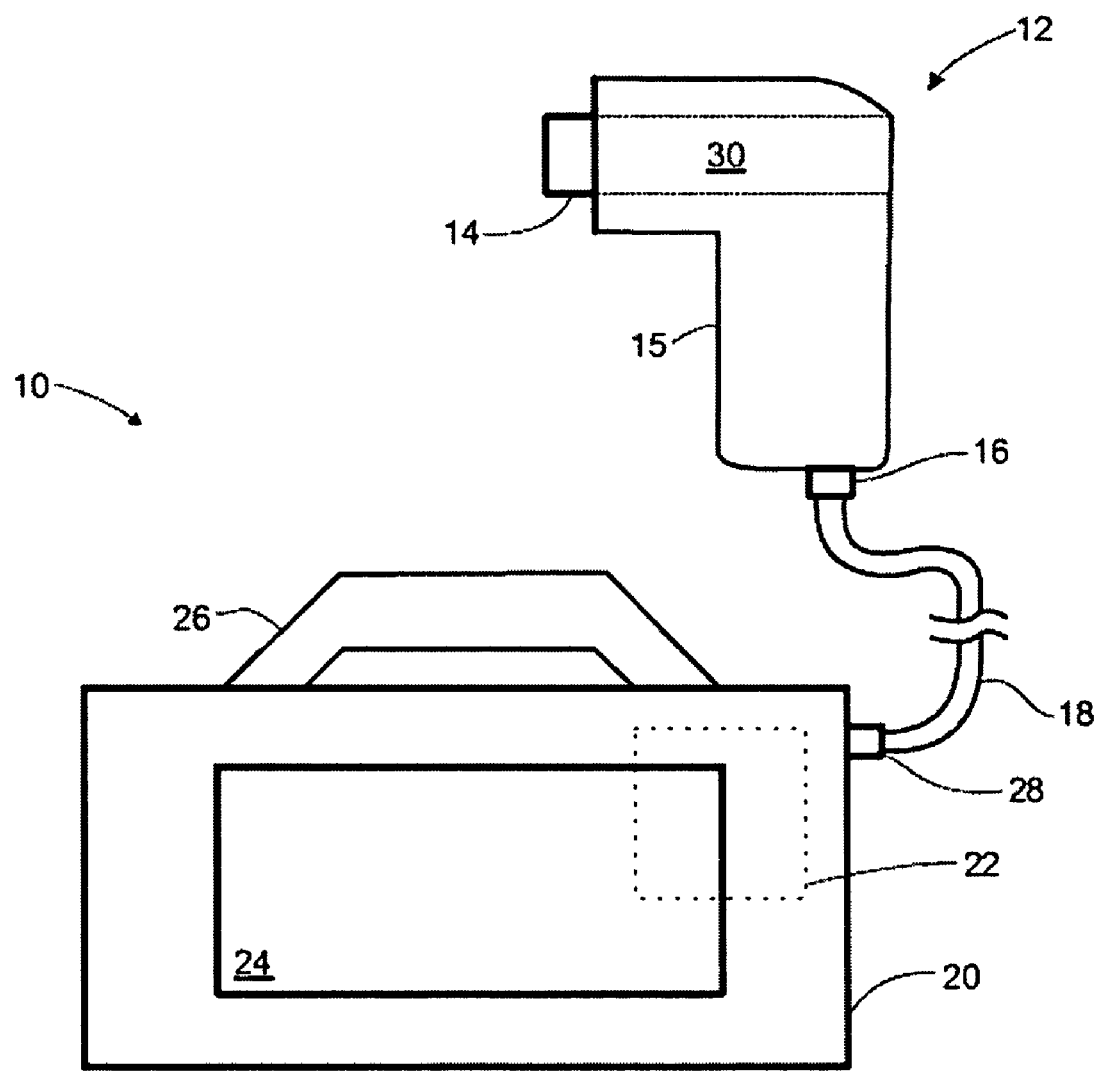
FIG. 1A is a schematic diagram of a system for aiding in the diagnosis of a physiological abnormality resulting in detectable, measurable variations in the contents and characteristics of breathed air in accordance with one embodiment of the present invention.

As shown in FIG. 1a, the system 10 of the preferred embodiment includes a handheld unit 12 defining an airway 30 (shown in phantom), wherein the airway 30 includes a plurality of sensors adapted to measure a plurality of parameters related to the presence of a physiological abnormality, such as a respiratory dysfunction. Further details of a preferred handheld unit 12 are described below with reference to FIG. 7. The system 10 further includes a control unit 20 remotely connected to the handheld unit 12. The control unit 20 includes a controller 22 (shown in phantom) adapted to receive input signals from the handheld unit 12 and remit output signals in response thereto. The output signals are usable by a user in determining the presence or absence of a physiological abnormality, such as a pulmonary dysfunction. The control unit 20 further can include a display 24 adapted to display the output signals to a user thereby facilitating data analysis. In addition to internally storing and displaying data, the control unit 20 also may provide ports (not shown), such as USB or Ethernet, for transferring data measurements to another device such as a computer, server, PDA, or printer device. In another embodiment, the control unit 20 may transfer data wirelessly to an external device.

In a variation of the preferred embodiment, the handheld unit 12 includes a first port 16 adapted to communicate with the control unit 20. Similarly, the control unit 20 can include a second port 28 that is adapted to communicate with the handheld unit 12. In one alternative embodiment, the first port 16 and the second port 28 are connected through wired means, which may include, for example, a cable 18 that is extendable therebetween. Alternatively, each of the first port 16 and the second port 28 may include wireless transmission and receiving antenna, wireless communications hardware, and wireless communications software that facilitate wireless communications of data between the handheld unit 12 and the control unit 20. In an alternative embodiment, instead of communicating with the control unit 20, the handheld unit 12 may communicate directly with an external device, and the external device may be one of any number of electronic devices having a memory portion and a processor portion for receiving and analyzing data transmitted through a wired or wireless communication means. These devices may include, for example, handheld personal computing devices, computer workstations and laptop computers.

In another variation of the preferred embodiment, the control unit 20 can include a handle 26 that is usable in the manual transport of the control unit 20. The handle 26 additionally can function as a receptacle for the handheld unit 12 when the latter is not in use. In this variation, the handheld unit 12 generally may define an elongated portion 15 that is perpendicular to the airway 30, wherein a user holds or grips the handheld unit 12 by the elongated portion 15 while breathing through the airway 30. In another variation of the preferred embodiment, the handheld unit 12 can include indentations or gripping surfaces to aid a patient in securing the handheld unit 12. Additionally, the elongated portion 15 of the handheld unit 12 may be rounded or bulbous so that a user may rest the handheld unit 12 comfortably against his chest for added stability during use.

The handle 26 can include one or more locking mechanisms to retain the handheld unit 12 when docked or otherwise physically connected to the control unit 20. Although FIG. 1a depicts the handle 26 as disposed on a top surface of the control unit 20, this configuration is changeable and the control unit 20 can bear the handle 26 on any other surface including, for example, a side surface. To that end, the second port 28 generally may exist on a surface distinct from that upon which the handle 26 is located, thus providing greater space for managing any cable 18 that connects the handheld unit 12 and the control unit 20.

Figure 1B:
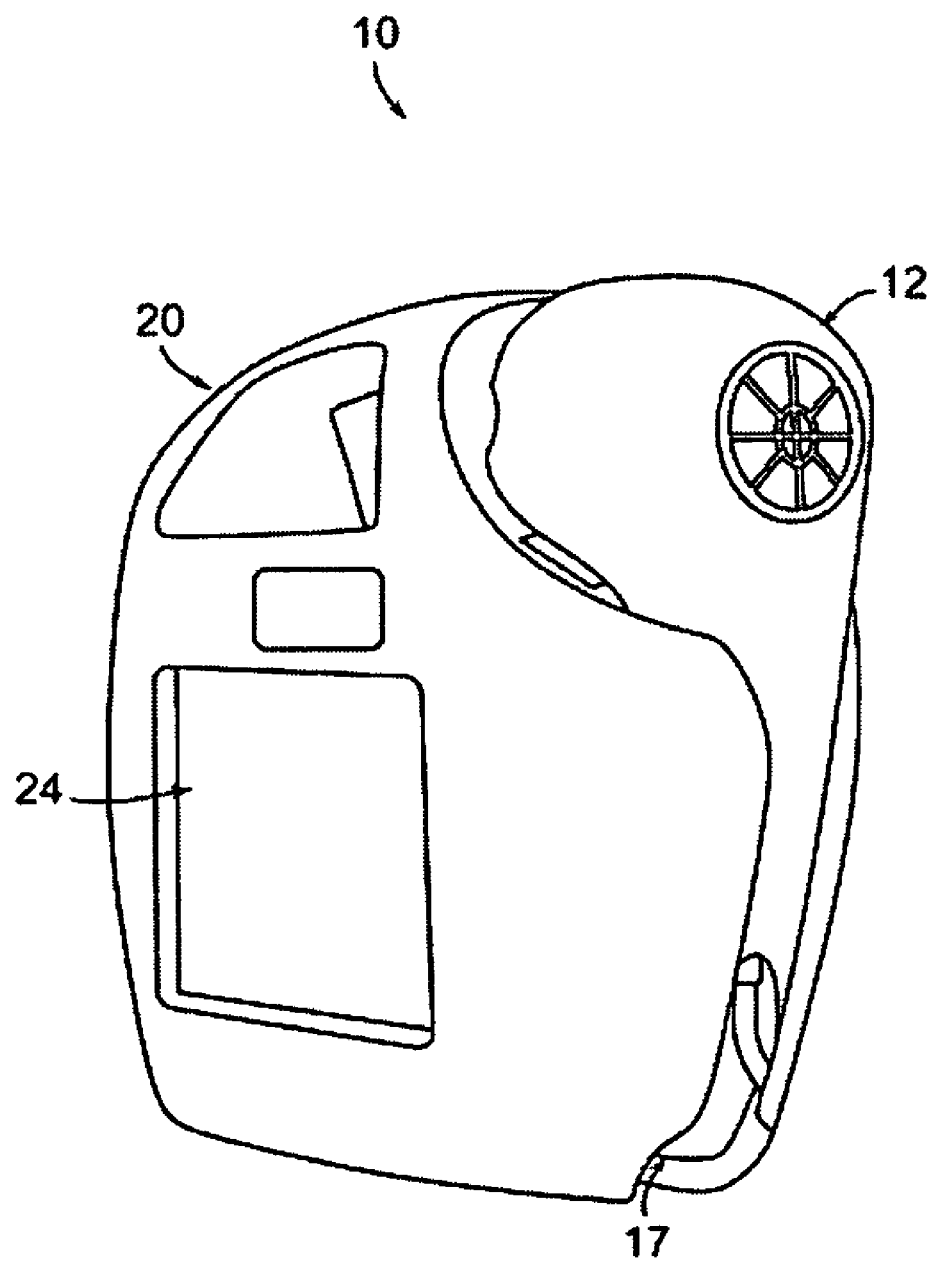
FIG. 1B is a depiction of a system for aiding in the diagnosis of a physiological abnormality resulting in detectable, measurable variations in the contents and characteristics of breathed air in accordance with an alternate embodiment of the present invention.
Figure 1C:
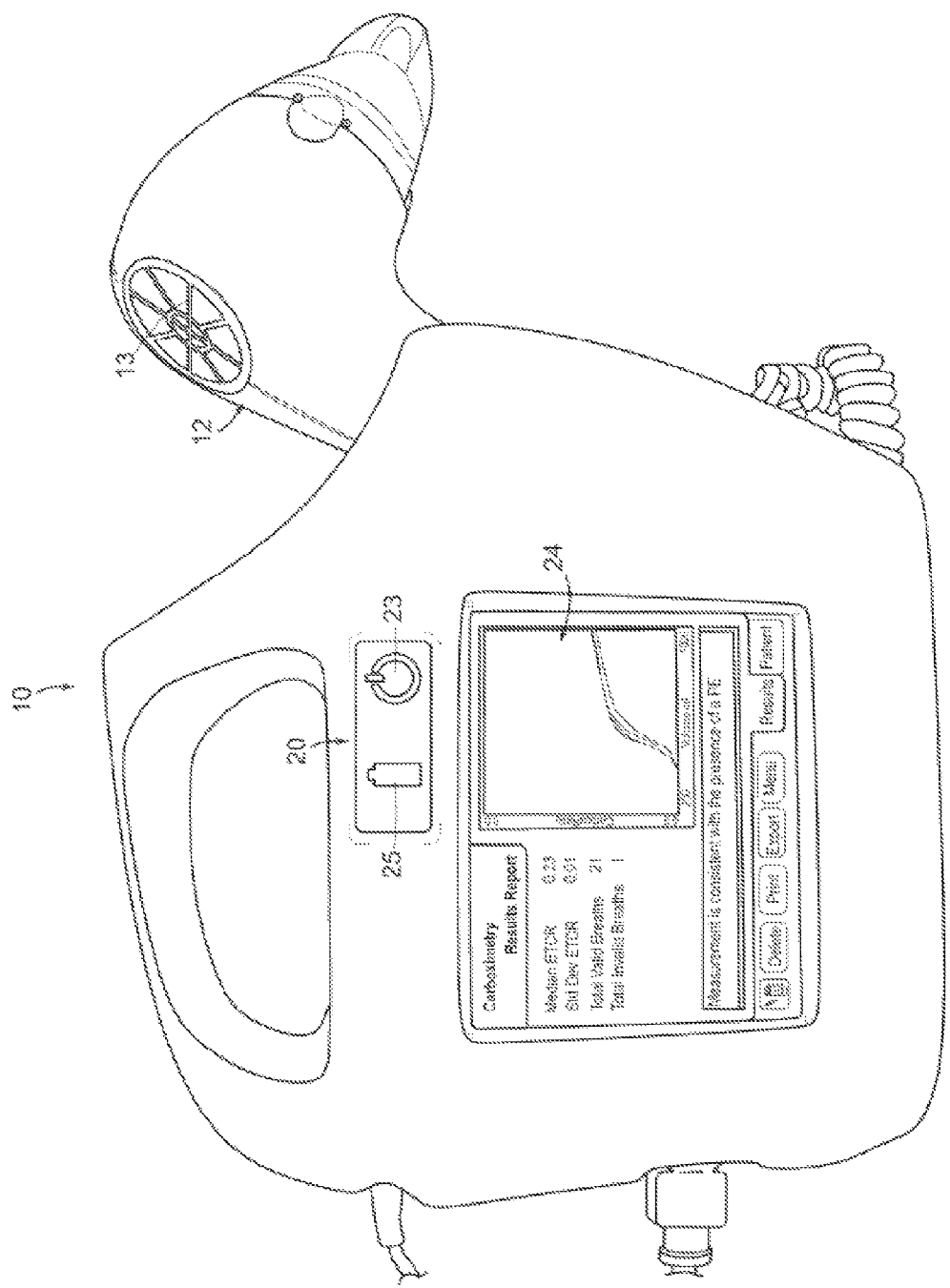
FIG. 1C is a depiction of a system for aiding in the diagnosis of a physiological abnormality resulting in detectable, measurable variations in the contents and characteristics of breathed air in accordance with an alternate embodiment of the present invention.
Figure 1D:
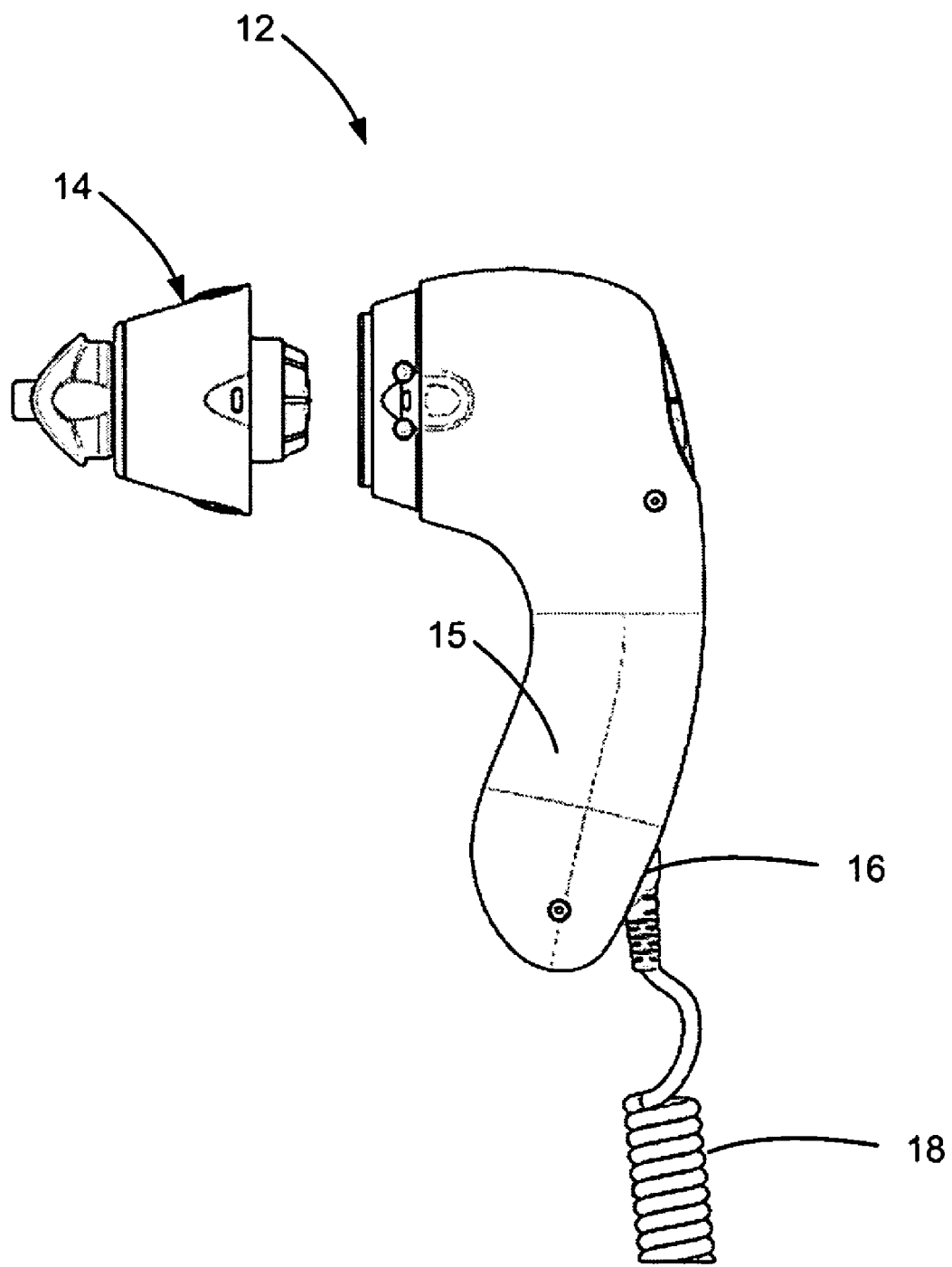
FIG. 1D is a depiction of a portion of a system for aiding in the diagnosis of a physiological abnormality resulting in detectable, measurable variations in the contents and characteristics of breathed air in accordance with an alternate embodiment of the present invention.

FIGS. 1b through 1d show an alternative embodiment of the control unit 20 and the handheld unit 12. Like parts are numbered the same between embodiments. As shown in FIG. 1b, the control unit 20 retains the handheld unit 12 in an upright position. In an alternative embodiment, the control unit 20 may retain the handheld unit in a prone position across the top of the control unit 20 in place of the handle 26. In this alternative embodiment, the control unit 20 may comprise a locking element for locking the handheld unit 12 in place for use as a handle 26.

FIGS. 1b and 1c depict an alternative embodiment of the handheld unit 12 which comprises a protective grating 13 over on end of the airway 30 so that the plurality of sensors remain protected from debris or objects that could cause damage.

As shown in FIG. 1b, the control unit 20 also may include a cable management system, such as a well 17 disposed within the control unit 20, for selectively containing the cable 18 during usage and storage of the system 10. The cable management system can include any mechanical or electromechanical means known in the art for minimizing the amount of cable 18 exposed during usage of the system 10. For example, the cable 18 may be a tension coil cable, like those used on telephone handsets, and when a user docks the handheld unit 12, the user aligns the tension coil cable 18 with the well 17 so that it contracts automatically into the well 17 in the control unit 20 for automatic storage.

The control unit 20 also may include a pole mount (not shown) for attaching to a bedrail or IV pole. The pole mount also may enable hanging the control unit 20 from a hook, such as an IV pole hook. Mounting the control unit 20 to a pole or hook enables a user to concentrate solely on breathing instead of simultaneously attempting to hold the control unit 20.

In an alternative embodiment, the control unit 20 also may contain a rechargeable battery of one of the many types well known in the art of rechargeable batteries for operating the system 10 free of any power cables. In this alternative embodiment, a user selectively may connect a power cable (not shown) to the control unit 20. The power cable may be one, for example, adapted to mate with an AC current standard wall outlet or a DC current automobile power outlet, for providing a charge to the rechargeable battery. The rechargeable battery then would store the charge for extended use apart from a power outlet. The control unit 20 also may operate during charging, with the power cable attached.

In addition to pole mounts and power outlets, an alternative embodiment of the control unit 20 also may comprise several additional elements, such a power indicator 23, a battery indicator 25 and cooling vents (no shown) for convective cooling of the central processing unit (not shown) contained within the control unit 20. Because the control unit 20 may stand upright or rest securely on its sides, the control unit 20 may further comprise raised ridges for keeping the cooling vents unobstructed when the control unit 20 rests with the cooling vents facing a surface.

In addition to the control unit 20 and the handheld unit 12, the system 10 further includes a removable mouthpiece 14 selectively connectable to the handheld unit 12. The removable mouthpiece 14 can include a filter adapted to substantially prohibit the passage of germs into the airway of the handheld unit. In one variation of the system 10 of the preferred embodiment, the removable mouthpiece 14 includes an integrated filtration media 70. As shown in FIGS. 8 through 13d, the removable mouthpiece 14 includes a substantially cylindrical body portion 60 defining a substantially cylindrical passageway 62 having a first end 64 and a second end 66. The removable mouthpiece 14 further includes a support member 68 disposed at a first end 64 of the body portion 60 and an integrated filtration media 70 connected to the support member 68.

The filtration media 70 is substantially conical and defines an open end 74 and a closed end 72. The filtration media 70 is disposed within the passageway 62 such that the open end 74 is substantially adjacent to the first end 64 of the body portion 60. The substantially conical filtration media 70 minimizes airflow resistance during both exhalation and inhalation by providing a large surface area through which air may flow. This design provides several benefits. Minimizing airflow resistance is of particular importance when patients suffer from respiratory distress because their airflow rates are often higher than those of patients breathing without respiratory distress. Minimizing airflow resistance also lessens a sensation of breathing through a device, which enables highly comfortable use and produces consistent readings for an accurate diagnosis.

The removable mouthpiece 14 is selectively connectable to a handheld unit 12 of the type described above, wherein the handheld unit 12 is adapted to measure a plurality of parameters that may be indicative of a number of physiological abnormalities, for example, a pulmonary dysfunction. The integrated filtration media 70 is adapted to substantially prohibit the passage of germs into the airway 30 of the handheld unit 12. To that end, the filtration media 70 may include certain antimicrobial coatings, fibers, compounds or compositions that are adapted to kill or occlude the passage of germs into the airway 30. In one embodiment of the present invention, the filtration media 70 comprises 3M® Filtrete® material and has an airflow resistance in the range of 0-4 cm $H_2O$ at 60 liters per minute of flow. Preferably, the filtration media 70 has an airflow resistance that is less than 2 cm $H_2O$ at 60 liters per minute of flow, and more preferably the filtration medial 70 has an airflow resistance equal to or less than approximately 1 cm $H_2O$ at 60 liters per minute of flow.

In addition to minimizing airflow resistance, as described above, the filtration media 70 further functions to minimize dead space volume within the removable mouthpiece 14 and within the airway 30 of the handheld unit 12. Minimization of the dead space volume provides a number of benefits, most notably increasing precision and reliability of measurements derived by the plurality of sensors disposed within the handheld unit 12. By minimizing the overall volume of air within the airway 30, the removable mouthpiece 14 improves the overall measuring capacity of the system 10 and further provides for a more reliable diagnosis of any physiological abnormality, such as, for example, a pulmonary dysfunction. Preferably, the mouthpiece occupies the entire volume of the airway 30 without touching the plurality of sensors. In the embodiment depicted in FIGS. 1b through 1d, the mouthpiece 14 occupies about 50% of volume in the airway 30.

Figure 7:
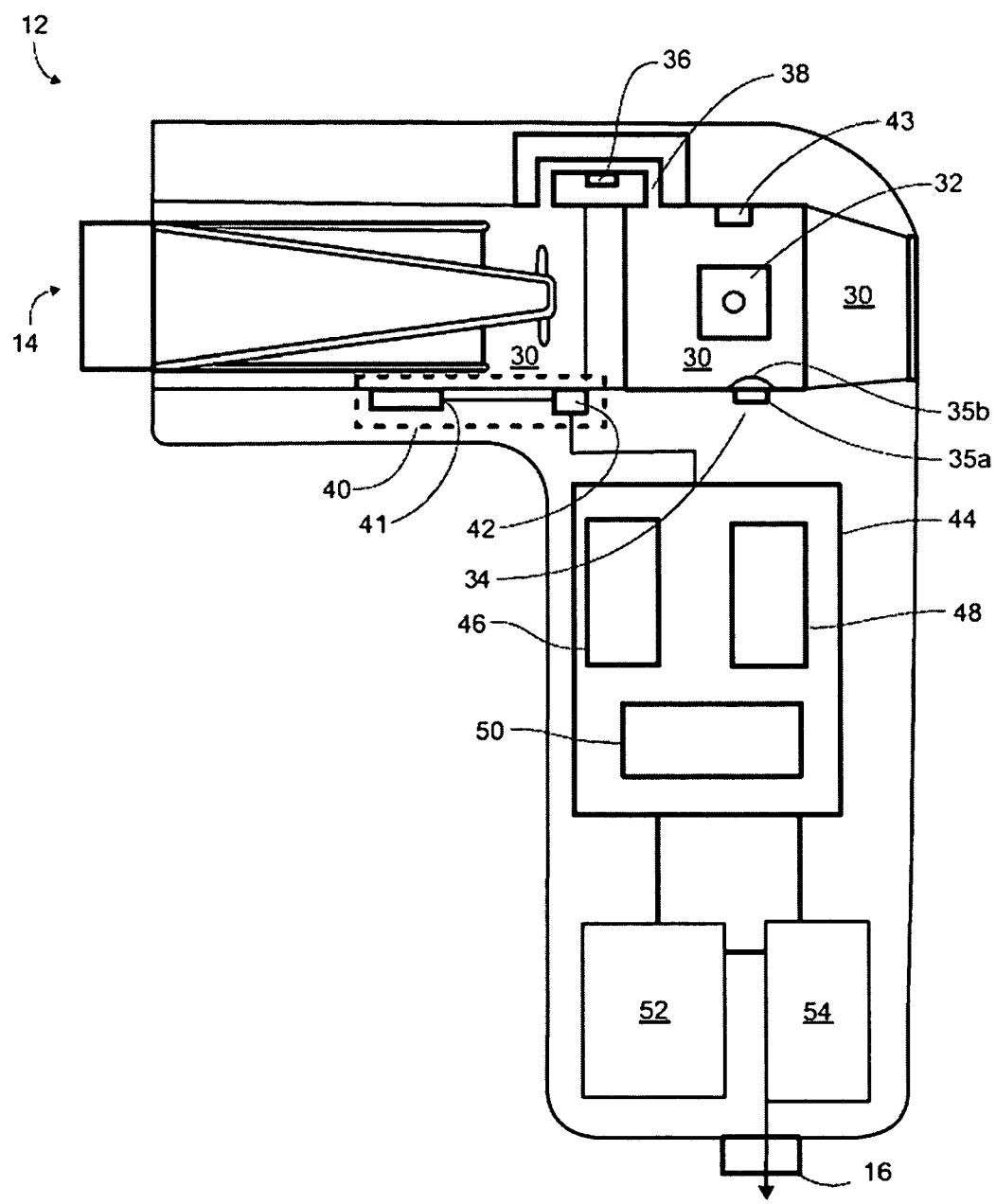
FIG. 7 is a schematic diagram of a handheld unit for aiding in the diagnosis of a physiological abnormality in accordance with one embodiment of the present invention.
Figure 8:
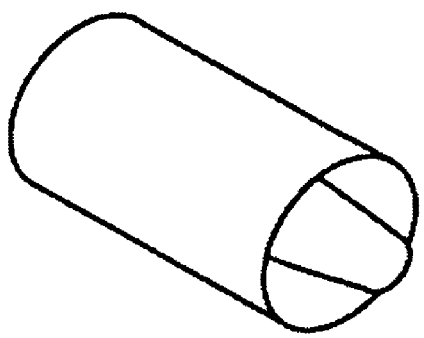
FIG. 8 is a rear perspective view of a removable mouthpiece for aiding in the diagnosis of a physiological abnormality in accordance with one embodiment of the present invention.
Figure 9:
FIG. 9 is a frontal view of a removable mouthpiece for aiding in the diagnosis of a physiological abnormality shown in FIG. 8.
Figure 10:
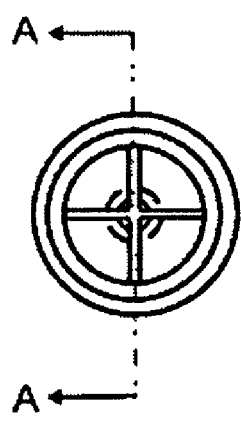
FIG. 10 is a rear view of a removable mouthpiece for aiding in the diagnosis of a physiological abnormality shown in FIG. 8.
Figure 11:
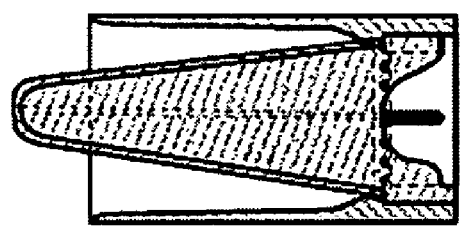
FIG. 11 is a cross-sectional view of a removable mouthpiece for aiding in the diagnosis of a physiological abnormality taken along section A-A shown in FIG. 10.

Although FIGS. 1 and 7 show the handheld unit 12 having a particular configuration, one skilled in the art would recognize readily that the handheld unit 12 having the above described airway 30 and removable mouthpiece 14 could adopt any number of ergonomic configurations. For example, the handheld unit 12 could be egg shaped or box shaped and provide finger grips for a secure one-handed or two-handed hold.

Additionally, in an alternate embodiment, the mouthpiece 14 could incorporate a mask for covering a user's airway. The mask easily could be designed to prevent air leakage, which could occur especially with users having facial hair that would prevent a precise seal between the mask and the user's face.

The description above generally describes the control unit 20 and handheld unit 12 portions of the system 10, and the following description provides further detail regarding these components of the present invention, starting with a description of the control unit 20.

Figure 2:
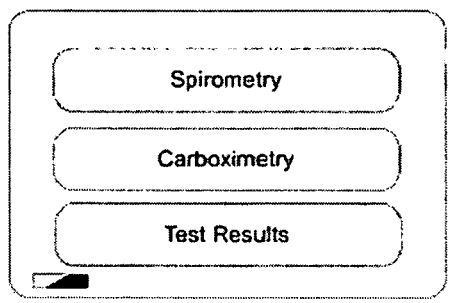
FIG. 2 is a representation of a display usable in the system for aiding in the diagnosis of a physiological abnormality in accordance with one embodiment of the present invention.
Figure 3A:
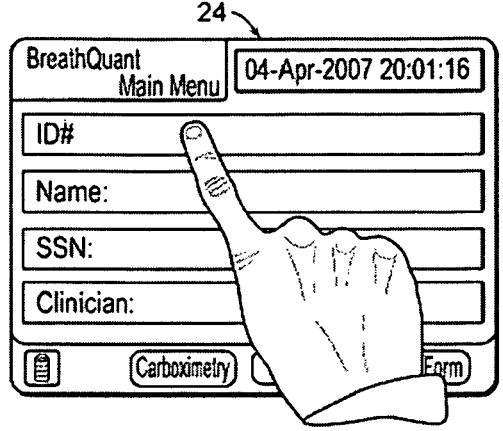
FIG. 3A is a representation of a display usable in the system for aiding in the diagnosis of a physiological abnormality in accordance with one embodiment of the present invention.
Figure 3B:
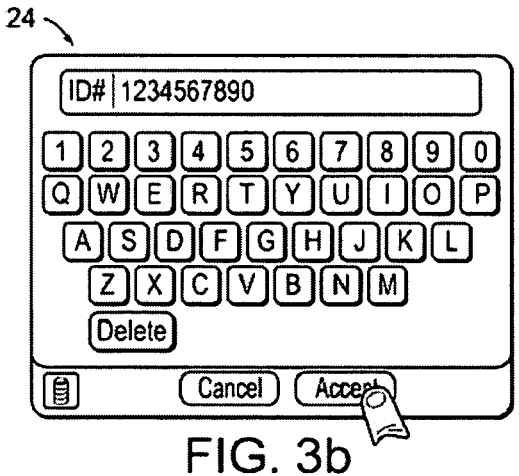
FIG. 3B is a representation of a display usable in the system for aiding in the diagnosis of a physiological abnormality in accordance with one embodiment of the present invention.
Figure 3C:
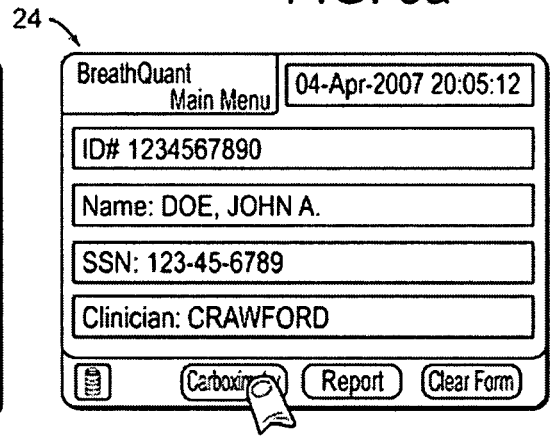
FIG. 3C is a representation of a display usable in the system for aiding in the diagnosis of a physiological abnormality in accordance with one embodiment of the present invention.
Figure 3D:
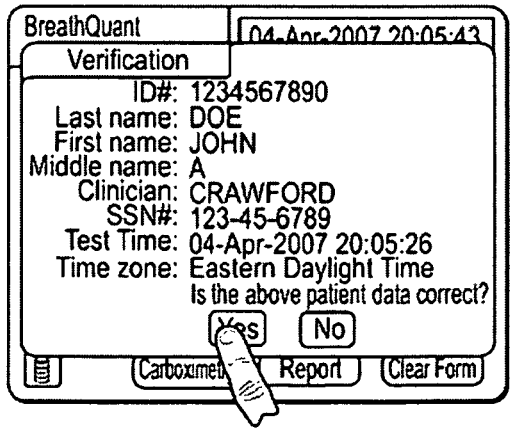
FIG. 3D is a representation of a display usable in the system for aiding in the diagnosis of a physiological abnormality in accordance with one embodiment of the present invention.
Figure 4:
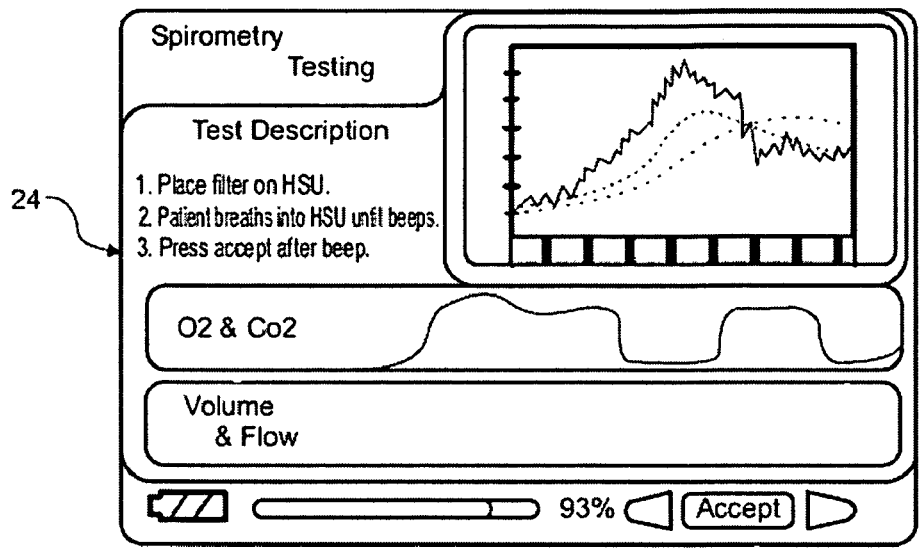
FIG. 4 is a representation of a display usable in the system for aiding in the diagnosis of a physiological abnormality in accordance with one embodiment of the present invention.
Figure 5:
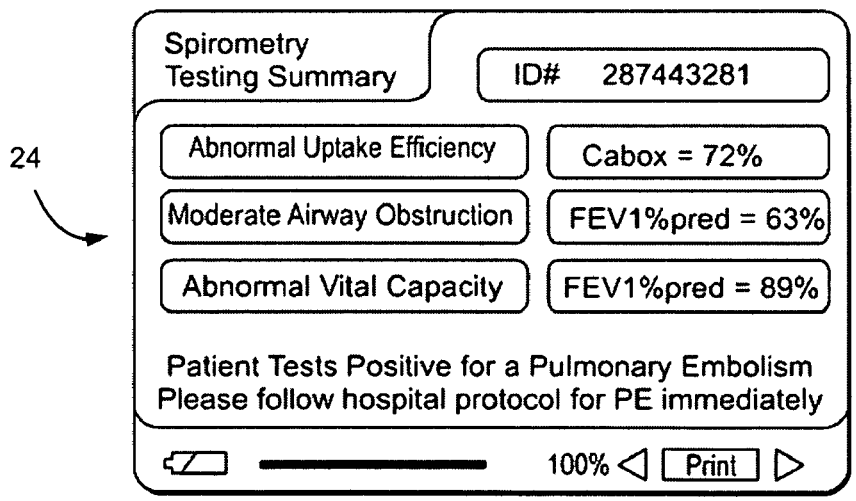
FIG. 5 is a representation of a display usable in the system for aiding in the diagnosis of a physiological abnormality in accordance with one embodiment of the present invention.

As shown in FIGS. 1a through 1c, the control unit 20 of the preferred embodiment includes a display 24 adapted to present output signals to a user. As shown in FIGS. 2a through 6d, the display 24 also may function as an interface between the control unit 20 and the user such that the user can input and/or select information to be viewed, tested, or summarized. The display 24 can include, for example, a touch screen or other interface that presents data and receives inputs from a user. As shown in FIG. 2, the display 24 may include a menu from which a user can select for presentation on the display 24 a type of test or a type of data, such as a spirometry reading or a carboximetry reading. As shown in FIG. 3a, the display 24 also can include an input panel that provides a means, such as a touch screen keypad, for entering information usable in identifying a patient.

Figure 6A:
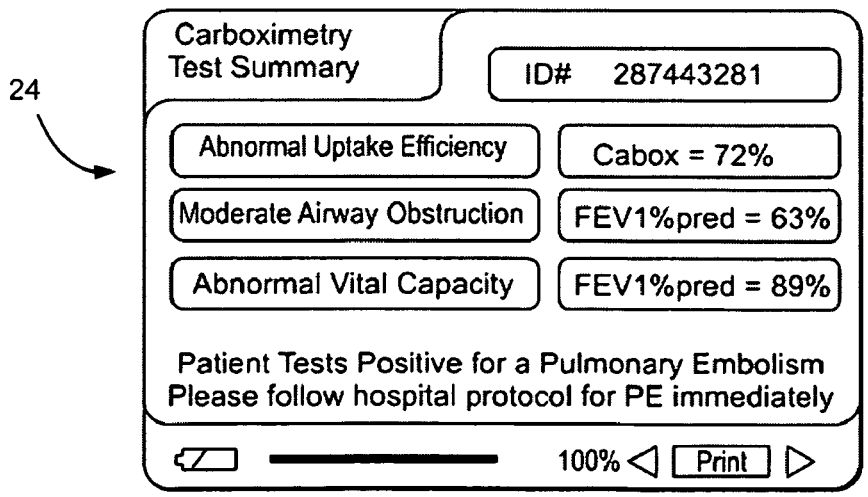
FIG. 6A is a representation of a display usable in the system for aiding in the diagnosis of a physiological abnormality in accordance with one embodiment of the present invention.
Figure 6B:
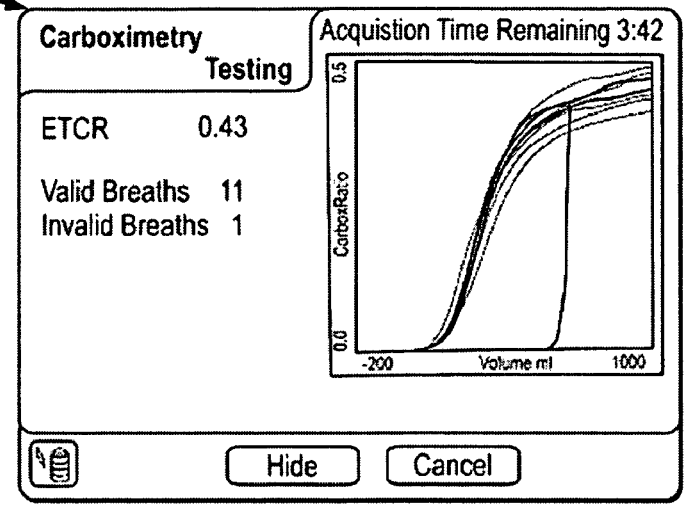
FIG. 6B is a representation of a display usable in the system for aiding in the diagnosis of a physiological abnormality in accordance with one embodiment of the present invention.
Figure 6C:
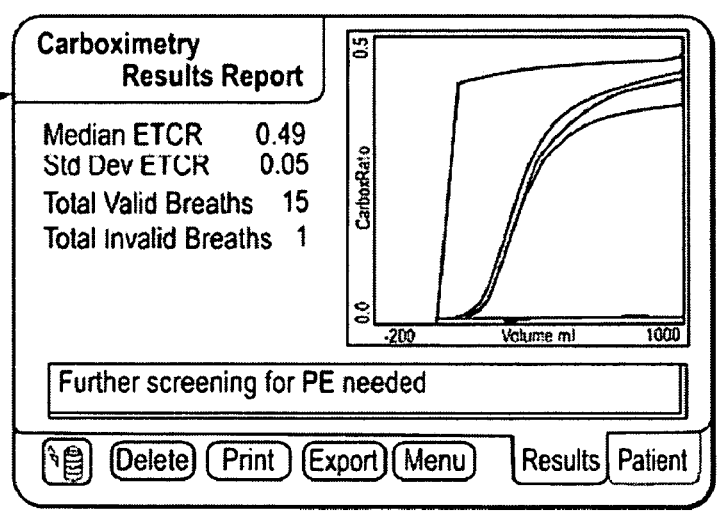
FIG. 6C is a representation of a display usable in the system for aiding in the diagnosis of a physiological abnormality in accordance with one embodiment of the present invention.
Figure 6D:
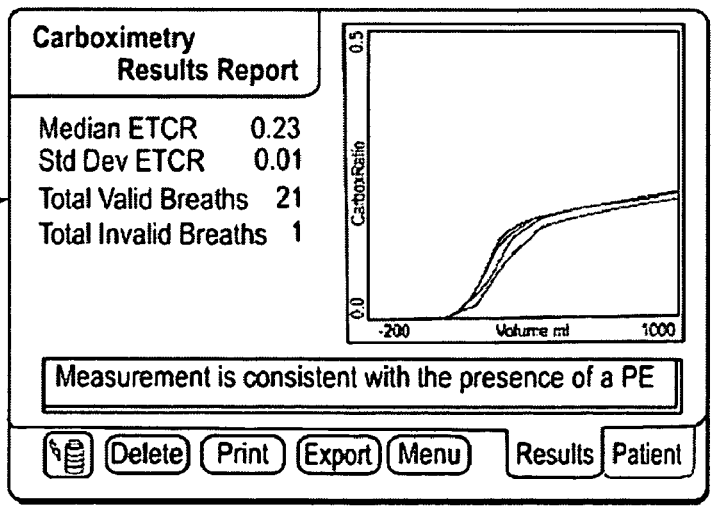
FIG. 6D is a representation of a display usable in the system for aiding in the diagnosis of a physiological abnormality in accordance with one embodiment of the present invention.

In other variations of the preferred embodiment, the display 24 can present graphic or tabular information regarding testing results for a particular patient. For example, FIGS. 4, 5 and 6 respectively illustrate a graphical representation of a patient's spirometry results, tabular information regarding the same, and tabular information regarding the same patient's carboximetry results. FIGS. 6b through 6d depict the display 24 presenting carboximetry results and an indication of whether a patient has a respiratory dysfunction, such as a pulmonary embolism, or whether further testing is required. An alternate embodiment of the present invention may provide an indication of the absence of a respiratory dysfunction such as a pulmonary embolism. The system 10 and the proprietary software therein can readily process data and format results for either graphical or tabular presentation, as well as any other format that is acceptable or preferable in the medical field.

The display 24 of the preferred embodiment further can interface with a user for other aspects of a patient's health that may relate to a physiological normality, such as a pulmonary dysfunction. For example, the display 24 can include menus and/or data representations related to a patient's heart rate, tidal volume, dead space volume, as well as any other diagnostic measure of a physiological abnormality, such as a pulmonary dysfunction. Additionally, the display 24 may provide an option for hiding the presentation of run time display data during patient use of the system 10. This option may prevent patients from experiencing any unnecessary stress caused by viewing their test results during testing. This option thus may increase the accuracy and repeatability of the diagnostic test by preventing patients from experiencing forms of biofeedback, or stress-induced fluctuations, which could occur from watching real-time and/or processed data during their test.

The present invention also includes a handheld unit 12 for aiding in the diagnosis of a physiological dysfunction. As shown in FIG. 7, the handheld unit of the preferred embodiment includes an airway 30 defined within the handheld unit and a plurality of sensors disposed within the airway. The plurality of sensors is adapted to measure a plurality of parameters related to the presence of a physiological abnormality. For example, sensors may measure parameters indicative of a respiratory dysfunction, parameters such as for example the oxygen and carbon dioxide content of a user's exhaled breath. The handheld unit 14 further includes a mouthpiece 14 selectively connectable to the handheld unit 12. The mouthpiece 14 can include a filter 70 adapted to minimize airflow resistance and substantially prohibit the passage of germs into the airway of the handheld unit.

In a variation of the preferred embodiment, the handheld unit 12 includes an oxygen sensor 34 having an emitter/sensor 35a and a lens 35b. The preferred oxygen sensor 34 is a combination of a light emitting diode (LED) and a photodetector that measures the reflectivity of light originating from the LED and reflecting off a selected surface. In most preferred embodiments, the LED emits light in or around the blue wavelengths that the lens 35b then directs onto a coated surface (not shown) that is reactive to oxygen. As the level of oxygen in the airflow varies, the fluorescence of the coated surface also varies, and the photodetector measures this variance. The system 10 uses known relationships between the reflective intensity of the coated surface and the measured photodetector values to compute an amount of oxygen in the airflow. Additionally, the coating on the sensor 35a is thermally stabilized, thereby improving measurement accuracy of the oxygen sensor 34.

The handheld unit 12 also can include a carbon dioxide sensor 32 that is disposed adjacent to the oxygen sensor 34 in the airway 30. The carbon dioxide sensor 32 is preferably a non-dispersive infrared sensor (NDIR), of the type known in the art.

According to one embodiment of the present invention, the oxygen sensor 34 and the carbon dioxide sensor 32 are arranged for minimizing the potential for error in the computation of the carbon dioxide to oxygen ratio of the airflow. More particularly, the oxygen sensor 34 and the carbon dioxide sensor 32 are arranged so as to be mutually orthogonal with a longitudinal axis of the airway 30. Additionally, because both sensors can be optical sensors, they can be arranged such that a first ray emanating from the oxygen sensor 34 and a second ray emanating from the carbon dioxide 32 sensor are substantially perpendicular. The first and second rays then define an imaginary plane that is substantially normal to the airflow passing through the airway 30.

This orientation provides a number of benefits, including synchronized data collection over a unique volume of air as it passes through the airway 30. Serial disposition of these sensors, as practiced in the state of the art, prevents each sensor from operating independently and simultaneously upon the same volume of air. That limitation creates an opportunity for changes in air temperature, flow direction, pressure or gaseous concentration to affect adversely the accuracy of measured values of oxygen and carbon dioxide. The present invention solves this problem through the aforementioned orthogonal orientation of the oxygen sensor 34 and the carbon dioxide sensor 32.

The handheld unit 12 of the present invention additionally can contain temperature and humidity control means 40 including at least a first thermometer 42 and a heating element 41, wherein the latter two elements preferably cooperate to maintain the temperature of the airway 30 at a predetermined level. Additionally, the handheld unit may incorporate a fan (not shown) for removing humidity from the airway 30, thereby improving sensor accuracy. A second thermometer 43 also can be disposed within the airway 30 for measuring an air temperature there. Variations in the temperature and relative humidity between inhaled air and exhaled air may cause unintended errors in the measurement of the carbon dioxide to oxygen ratios as measured by the present invention. The software portion (not shown) existing within the system also executes a thermal-correction algorithm on the CPU (not shown). This algorithm improves performance of the oxygen sensor 35 by reducing thermal variation in the oxygen sensor 35 reading and thereby reduces thermal error by a factor of about 2. By warming the airway 30, the heating element 41 thermally stabilizes air flowing over any airway sensors, such as the oxygen sensor 35 and the carbon dioxide sensor 32, by normalizing the relative humidity and temperature gradient over each respiration cycle. The heating element 41 also prevents condensation from forming on critical sensing surfaces. Elevating the temperature of the airway sensors to something higher than the temperature of the humidified air exhaled through the airway 30 prevents condensation from interfering with proper operation. The conical filtration media 70 also may consist of a material suitable for entrapping humidity, thereby blocking condensation from entering the airway 30.

The temperature control means 40 of the present invention is adapted for maintaining the temperature of the airway 30 at a range between thirty-three and forty-three degrees Celsius. More preferably, the temperature control means 40 of the present invention is adapted for maintaining the temperature of the airway 30 at approximately thirty-eight degrees Celsius. The temperature control feature of the present invention provides a number of benefits including warming the inhaled air so as to decrease the temperature gradient over the respiration cycle of a user and increasing the sensitivity of the oxygen sensor 34 and the carbon dioxide sensor 32 by normalizing the relative humidity and temperature gradient over the respiration cycle. The software portion (not shown) existing within the system 10 also monitors the temperature of the temperature control means 40 and prevents use of the system 10 in the event that the temperature deviates from a range determined to be acceptable for either sensor calibration accuracy or condensation prevention.

In another variation of the preferred embodiment, the handheld unit 12 can include a bypass channel 38 that connects to the airway 30. The bypass channel 38 functions to remove a minimal portion of the airflow from the airway 30 for the purposes of measuring one or more parameters associated with the airflow. For example, the bypass channel 38 may contain one or more sensors for measuring one or more of the temperature, pressure, carbon dioxide content, or oxygen content of the airflow. Additionally, the bypass channel 38 may contain a thermometer.

In a variation of the preferred embodiment having the oxygen sensor 34 disposed within the bypass channel 38, the bypass channel 38 serves an added benefit of preventing stray light from reaching the oxygen sensor and corrupting measurement accuracy. In other variations of the preferred embodiment, the handheld unit 12 can include a second bypass channel (not shown) that is located opposite or adjacent to the bypass channel 38. The second bypass channel also may contain one or more sensors. For example, the second bypass channel may contain an oxygen sensor 34 of the type described above in order to prevent ambient light from entering the airway 30 and corrupting the oxygen sensor 34. An additional bypass channel (not show) may provide a bypass to ambient air and thus conduct fresh air into the airway 30 during inhalation. A plurality of bypass channels 38 may exist containing any number of sensors and each of those bypass channels 38 may be arranged in any orientation with respect to one another.

In a preferred embodiment, a first bypass channel 38 contains an oxygen sensor and a second bypass channel (not shown) contains a volumetric airflow sensor. The flow within the bypass channel 38 is in fluid communication with the airway 30. As shown in FIG. 7, a volumetric airflow sensor 36 disposed within the bypass channel 38 measures the flow within the handheld unit 12. This sensor may be any volumetric airflow sensor known in the art, such as a delta pressure sensor, a hot-wire anemometer, or a turbine tachometer device. Measuring airflow allows the system 12 to calculate a volume of air flowing into and out of a user's lungs. This derived measurement is critical in identifying any number of physiological abnormalities, for example, a respiratory dysfunction such as a pulmonary embolism.

Additional ambient sensors (not shown) located within the elongated portion 15 of the handheld unit 12 measure ambient temperature, pressure and humidity for calibrating the system 10. An open air flow channel (not shown) exits within the elongated portion 15 of the handheld unit 12 such that ambient air flows into the elongated portion 15 where the ambient sensors lie. This ensures a homogenous psychrometric condition of the outside ambient air and the air in contact with the ambient air sensors. A thermal barrier (not shown) exists between the portion of the handheld unit 12 containing the heating element 41 and the portion of the handheld unit containing the ambient air sensors. This thermal barrier reduces any potential for error in ambient air sensor readings caused the heating element 41 potentially heating the ambient air sensors above the temperature of the ambient air outside of the handheld unit 12. These additional sensors in combination with sensors in the airway 30 and the bypass channel 38 enable a single point calibration correction. This calibration is a psychrometric correction that requires no external, active calibration using calibration gases. The control unit 20 then takes measurements from the sensors in the bypass channel 38 and compares those to corrected values of known molecular concentrations of oxygen and carbon dioxide in ambient air. These known ambient concentrations are corrected for ambient temperature, pressure and humidity as measured by the additional sensors positioned within the elongated portion 15. The system 10 uses these derived values to calibrate the oxygen sensor 34 and the carbon dioxide sensor 32. The software portion (not shown) existing within the system 10 also monitors the ambient sensor measurements and prevents use of the system 10 in an event that any ambient sensor measurement deviates from a range determined to be acceptable for either sensor calibration accuracy or general operation.

In one embodiment, calibration also includes the step calibrating the airflow sensor 36 by restricting airflow from airway 30. A user may restrict airflow by docking the handheld unit 12 on the controller unit 20 which has a low pressure seal thereon for contacting the handheld unit 12 and sealing the airway 30 on one end. The geometry of the handheld unit 12 enables correct positioning and a proper seal when docked on the control unit 20. Restricting airflow enables calibration of the volumetric airflow sensor 36 in this zero-flow condition. Alternatively, connecting removable mouthpiece 14, with a filter 70 disposed therein, to the handheld unit 12 restricts airflow with the airway 30 such that accurate calibration is possible without docking the handheld unit 12 on the control unit 20.

In one embodiment, runtime calibration of the handheld unit 12 occurs automatically prior to each use. This runtime calibration adjusts sensor measurement for potential drift and/or change over time. Prior to running the carboximetry runtime calibration, the controller unit 20 instructs an operator to ensure proper installation of the removable mouthpiece 14. The controller unit also instructs the operator to avoid moving the handheld unit 12 and breathing into the handheld unit 12, and to ensure fresh ambient air is in the airway 30. Once and operator acknowledges the instructions, the system 10 runs a carboximetry runtime calibration. The control unit 20 analyzes collected data and determines whether a sensor calibration is necessary or whether a fundamental sensor error has occurred. These determinations depend on flow conditions and expected concentrations of oxygen and carbon dioxide.

Turning now back to the airway 30 of the handheld unit 12, the present invention further includes a removable mouthpiece 14 usable in the detection of a physiological abnormality, symptoms of which manifest in measured components of a breath of air. As shown in FIGS. 8 through 11, the removable mouthpiece 14 includes a substantially cylindrical body portion 60 defining a substantially cylindrical passageway 62 having a first end 64 and a second end 66. The removable mouthpiece 14 further includes a support member 68 disposed at a first end 64 of the body portion 60 and an integrated filtration media 70 connected to the support member 68. The filtration media 70 is substantially conical and defines an open end 74 and a closed end 72. The orientation of the filtration media 70 within the passageway 62 is such that the open end 74 is substantially adjacent to the first end 64 of the body portion 60.

The removable mouthpiece 14 is selectively connectable to a handheld unit 12 of the type described above, wherein the handheld unit 12 is adapted to measure a plurality of parameters that may be indicative of a physiological abnormality. The integrated filtration media 70 substantially prohibits the passage of germs into the airway 30 of the handheld unit 12. To that end, the filtration media 70 may include certain antimicrobial coatings, fibers, compounds or compositions that are adapted to kill or occlude the passage of germs into the airway 30.

The filtration media 70 further functions to minimize the dead space volume within the removable mouthpiece 14 and within the airway 30 of the handheld unit 12 and, most importantly, because of its substantial surface area available for airflow exchange, the filtration media 70 minimizes airflow resistance during both exhalation and inhalation. Minimizing the dead space volume while minimizing airflow resistance provides a number of benefits, most notably increased precision and reliability of measurements derived by the plurality of sensors disposed within the handheld unit 12. In one embodiment, the diameter ratio of the filtration media 70 diameter at the closed end 72 to the filtration media 70 diameter at the open end 74 is between 1:2 and 1:4 and more preferably is approximately 3:8. Based on this preferred diameter ratio, an optimal range of ratios of preferred length of the filtration media 70 to the closed end 72 diameter of the filtration media 70 is between 4:1 and 5:1. These dimensions provide low resistance of the filtration media 70 while occupying a volume measuring close to half of the airway 30.

By minimizing the overall volume of air located within the airway 30, the removable mouthpiece 14 improves the overall measuring capacity of the system 10 and provides a more reliable diagnosis of any physiological abnormality. With dead space volume minimized, the system 10 requires that a user produce only a minimal volume per breath to properly and consistently operate the sensors of the present invention. With airflow resistance minimized, a user may breathe more comfortably through the handheld unit 12 thereby producing more consistent and accurate results. This increased control and precision of relevant measurement variables (flow, temperature, oxygen, carbon dioxide, and pulse rate) helps to assure an accurate and predictive diagnosis of any physiological abnormalities detectable in a quantity of breathed air, abnormalities such as respiratory dysfunction.

The removable mouthpiece 14 mates with the airway 30 without a need for additional tools. In one embodiment, the removable mouthpiece 14 maters with the handheld unit 12 under no more than 1.5 kg of insertion force and no more than 0.25 Nm of rotational moment during either installation or removal. Additionally, in one exemplary embodiment, the assembled removable mouthpiece 14 and handheld unit 12 maintain a static low-pressure seal of at least 6 cmH2O for no less than 5 minutes, losing no more than 0.05 cmH2O of pressure while subject to a static load no less than +/−1.2 kg applied in the following two orientations: 1) along the longitudinal axis of the airway 30 and 2) perpendicular to the longitudinal axis of the airway 30 at three distinct, equally spaced points around the diameter of the disposable inlet, at a distance no grater than 1 cm from the inlet of the removable mouthpiece 14. Under these conditions, the removable mouthpiece 12 shall not break or form a crack when subject to a static load no less than +/−5 kg applied in the following orientations: 1) along the longitudinal axis of the airway 30, 2) perpendicular to the longitudinal axis of the airway 30 at three distinct, equally spaced points around the diameter of the disposable inlet, at a distance no grater than 1 cm from the inlet of the removable mouthpiece 14, 3) rotational moment perpendicular to the longitudinal axis of the airway 30, applied at a distance no great than 1 cm from the inlet of the removable mouthpiece 14, and 4) rotational moment perpendicular to the longitudinal axis of the airway 30, applied within 0.5 cm of the largest cross section diameter of the removable mouthpiece 14

FIGS. 12a through 13d show views of alternative embodiments of the removable mouthpiece 14. As shown in detail in FIGS. 12a and 12b, these alternative embodiments of the removable mouthpiece 14, comprise a flared, substantially conical spitguard 85 that protects and maintains cleanliness of the handheld unit 12 between users. The spitguard 85 preferably provides diametrically opposed finger grips 90 for assisting a user with inserting the removable mouthpiece 14 into the handheld unit 12. Further, as shown in FIGS. 13b and 13c, one alternative embodiment of the removable mouthpiece 14 may provide key indentations 92 for mating with raised ridges on the handheld unit 12 so that the mouthpiece 14 is properly oriented within the airway 30.

This alternative embodiment of removable mouthpiece 14 requires proper orientation because of a flange unit 95 designed for comfortably holding a user's mouth open to provide a free flow of air while enabling a comfortable seal. The flange unit 95 has thereon bite tabs 100, 105 on which a user comfortably may rest his teeth. Because the tabs 100, 105 are spaced apart from one another, a user's mouth then remains spaced apart. The flange unit 95 also comprises a lip rest 110 against which a user comfortably may rest his lips to provide a proper seal and prevent loss of airflow through the handheld unit 12. Both the flange unit 95 and an internal seal 115 that helps the mouthpiece 14 engage securely with the handheld unit 12 may be formed of a thermoplastic elastomer (TPE), such as Mediprene®, which has a high biocompatibility and lessens the potential for an allergic response in a user. Additionally, the internal seal 115 may exist on the mouthpiece either within the mouthpiece 14 as depicted clearly in FIG. 12b or at the end of the mouthpiece 14 as depicted in FIG. 13a.

Figure 12A:
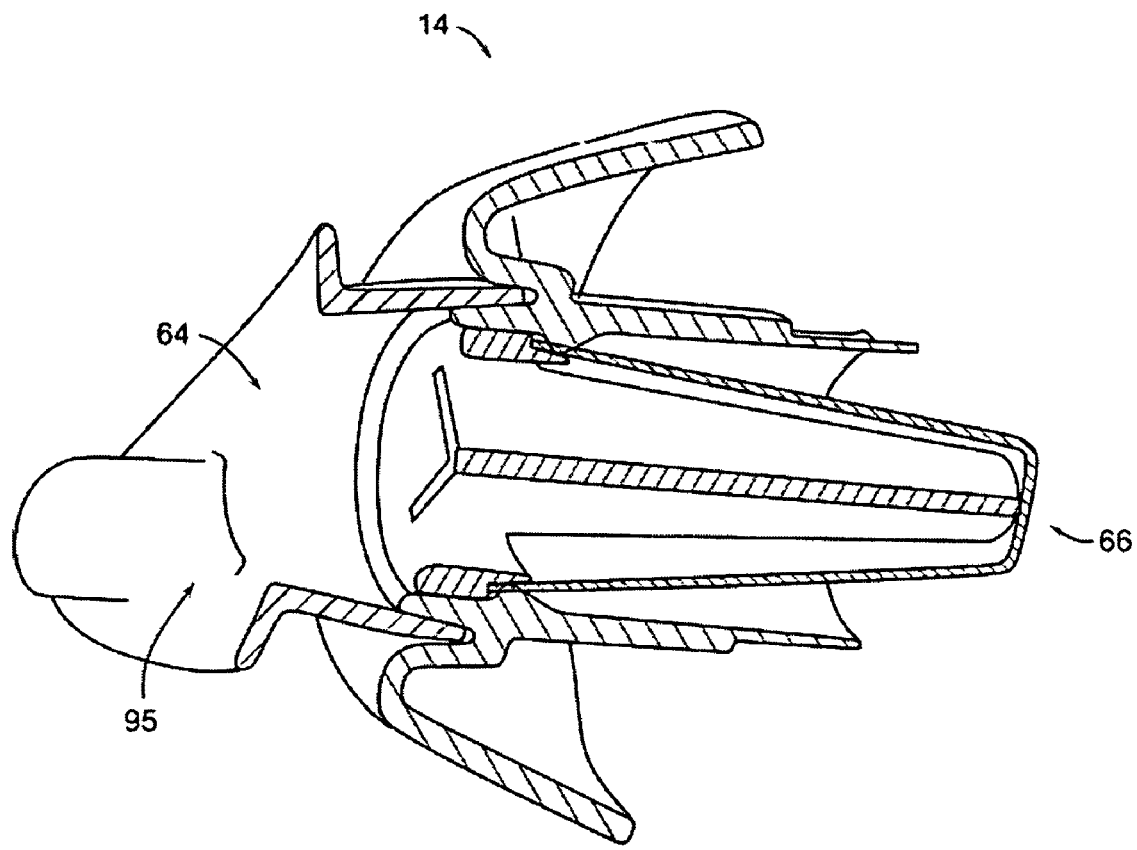
FIG. 12A is a cross-sectional view of an alternative embodiment of a removable mouthpiece for aiding in the diagnosis of a physiological abnormality.
Figure 12B:
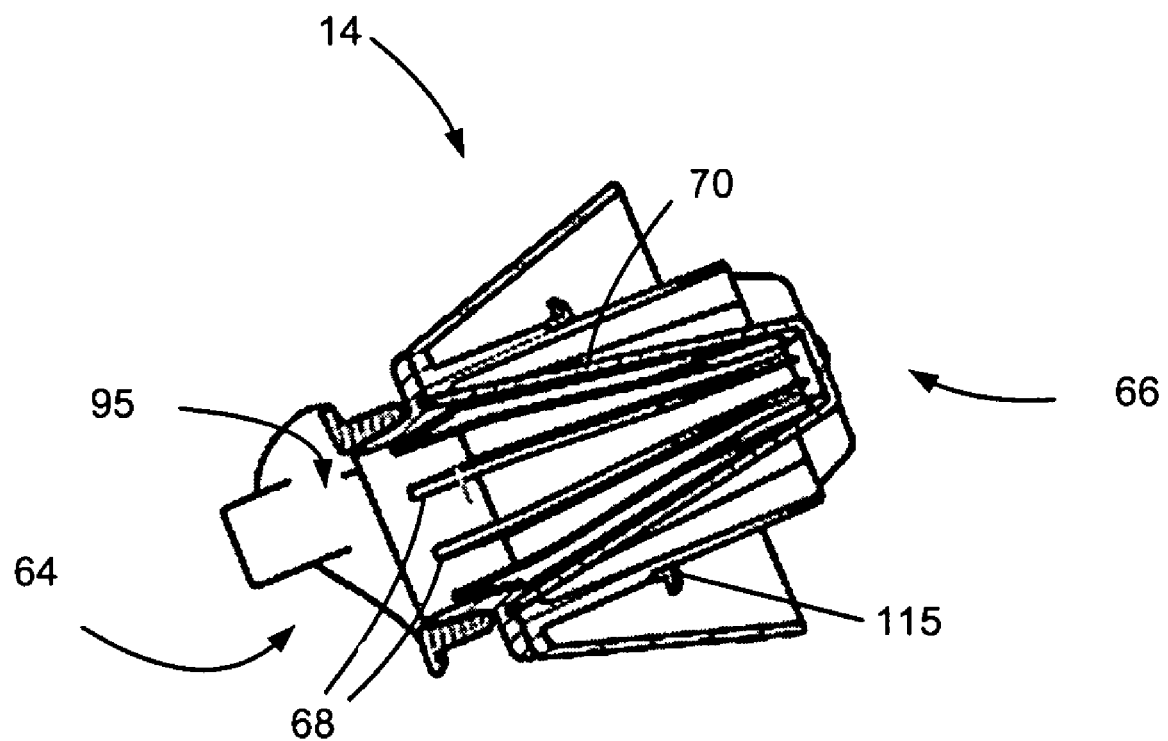
FIG. 12B is a cross-sectional view of another alternative embodiment of a removable mouthpiece for aiding in the diagnosis of a physiological abnormality.
Figure 12C:
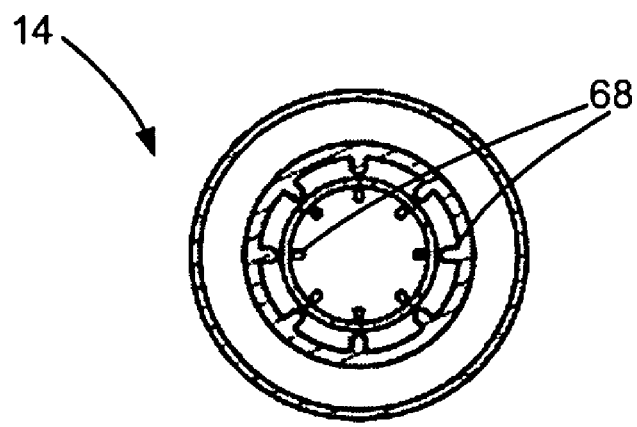
FIG. 12C is an end view of an alternative embodiment of a removable mouthpiece shown in FIG. 12*b* for aiding in the diagnosis of a physiological abnormality.
Figure 12D:
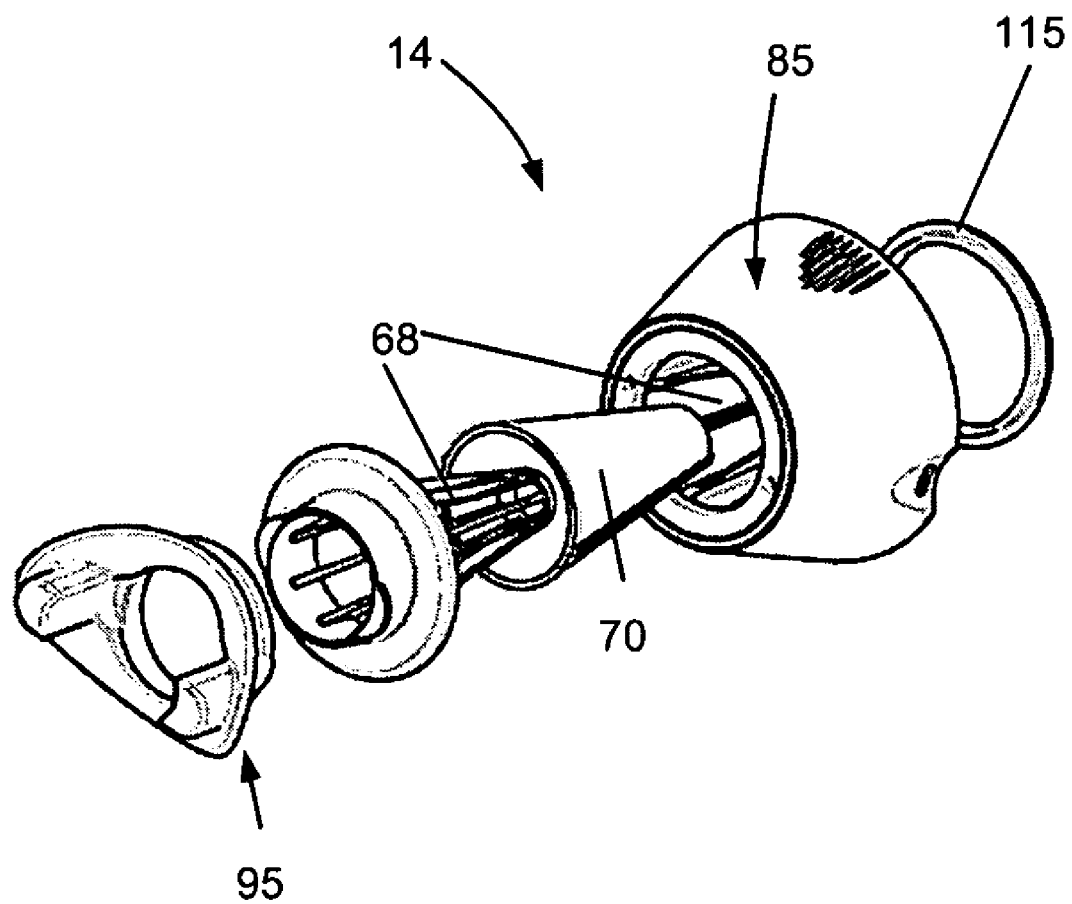
FIG. 12D is an exploded view of an alternative embodiment of a removable mouthpiece shown in FIG. 12*b* for aiding in the diagnosis of a physiological abnormality.
Figure 13A:
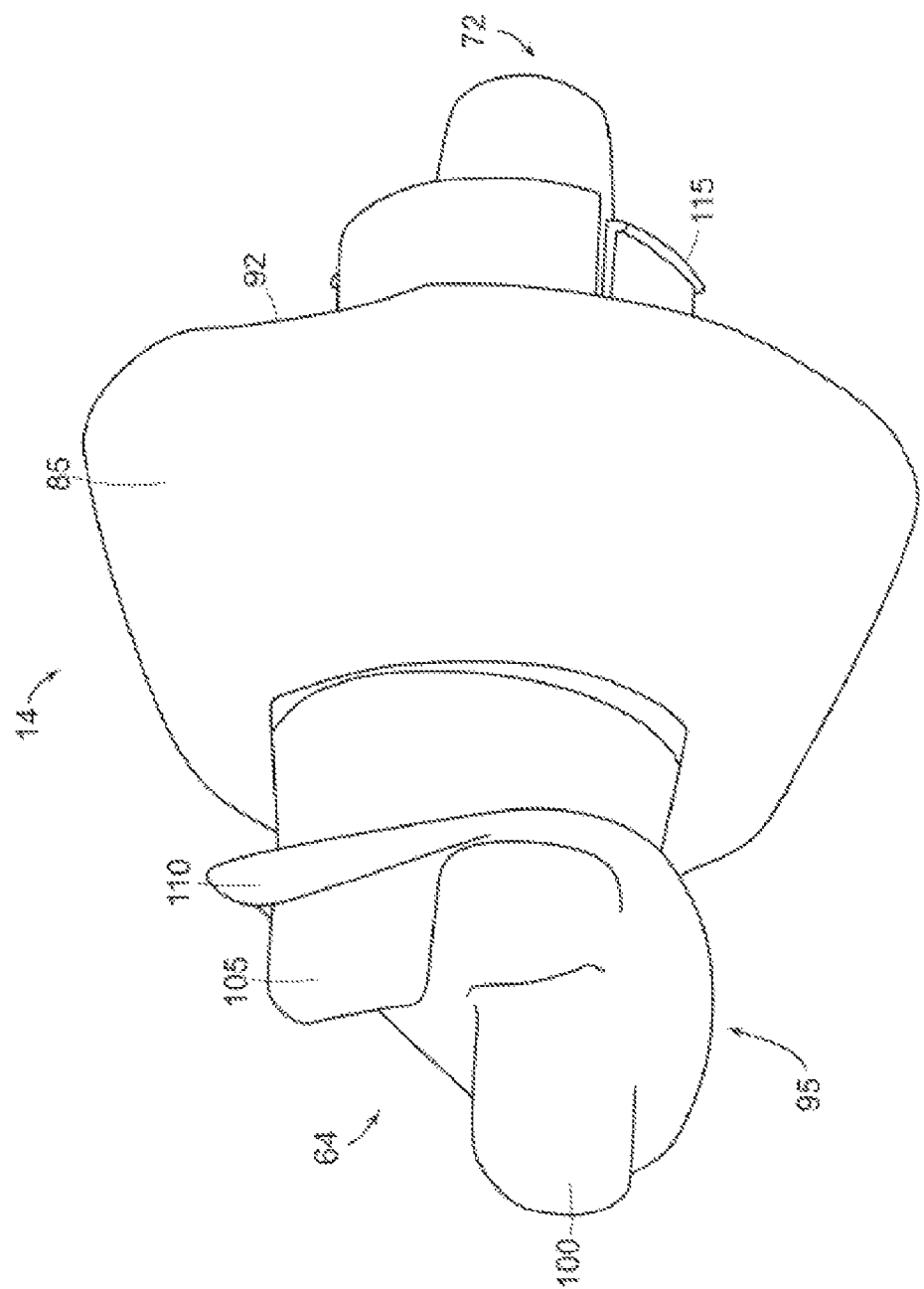
FIG. 13A is a side view of an alternative embodiment of a removable mouthpiece for aiding in the diagnosis of a physiological abnormality.
Figure 13C:
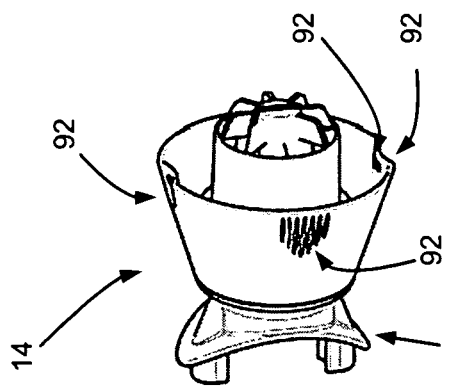
FIG. 13C is another perspective view of an alternative embodiment of a removable mouthpiece shown in FIG. 13b.
Figure 13D:
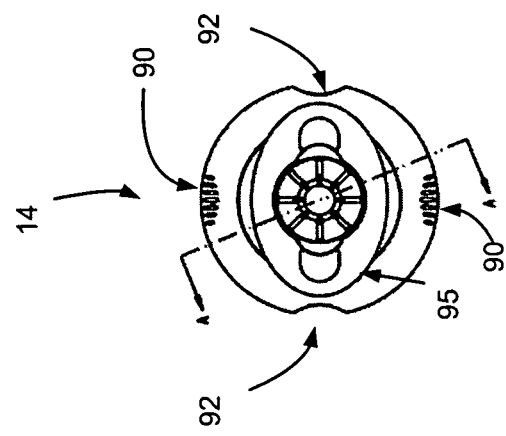
FIG. 13D is an end view of an alternative embodiment of a removable mouthpiece shown in FIG. 13b.
Figure 13B:
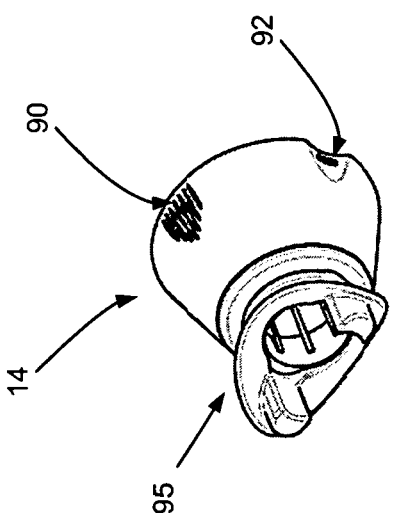
FIG. 13B is a perspective view of another alternative embodiment of a removable mouthpiece.

In addition to the flange unit 95 and key indentations 92, FIGS. 12b through 12d depict an embodiment of the mouthpiece 14 having a filtration media 70 supported by a support member 68 comprising a plurality of fins for surrounding and supporting both internal and external surfaces of the filtration media. The support member 68 of this embodiment of the mouthpiece 14 thereby constrains the filtration media 70 and prevents the filtration media 70 from ballooning out or collapsing and cutting off airflow during exhalation and inhalation respectively.

The number of fins comprising the support member 68 and their placement directly effect resistance. Too many fins would increase resistance too much and too few fins would leave the filtration media 70 unsupported. In the embodiment depicted FIGS. 12b through 12d and FIGS. 13b through 12d, the support member 68 comprises 8 fins arranged symmetrically and spaced evenly about the substantially conical filtration media 70; Any number and arrangement of fins is possible. The size and shape of the fins is also flexible such that the fins may be sculpted to aid airflow into the filtration media 70. In alternative embodiments, instead of providing fins, the support member 68 may comprise a mesh or mesh-like structure for constraining the filtration media. Alternatively, the support member 68 may support only the exterior surface of the filtration media 70 and the filtration media 70 may be pleated to resist ballooning and collapsing during exhalation and inhalation.

Use of a disposable removable mouthpiece 14 in the system 10 described above permits a user to reuse the handheld unit 12 on different patients without the need for any sterilization or cleaning procedures. A user of the system 10 and handheld unit 12 of the present invention readily can affix a new, sterilized removable mouthpiece 14 to the handheld unit 12 prior to use on a new patient. Following testing of a patient, the user can simply remove and discard the removable mouthpiece 14, including the filtration media 70, and return the handheld unit 12 to its proper storage location. Use of the removable mouthpiece 14 saves a user any time that otherwise would be dedicated to cleaning or sterilizing the handheld device 14. As such, the user can have more time to dedicate to treatment and diagnosis of potential physiological abnormalities, such as pulmonary dysfunctions, in one or more patients.

Integration of the filtration media 70 into the removable mouthpiece 14 also can save significant costs in the design and production of the system 10 and handheld unit 14 of the present invention. No need exists for cleaning or replacing both a mouthpiece and a filter. The present invention provides a removable mouthpiece 14 that a user can secure and remove as needed on a single-use basis. Manufacture of the removable mouthpiece 14 also is simplified because the filtration media 70 is integrated within the mouthpiece 14. No need exists for designing or manufacturing special surfaces, contours or features that would permit the cleaning of the removable mouthpiece 14 or the removal of the filtration media 70. Accordingly, the removable mouthpiece 14 is manufacturable at a lower cost than a more traditional, reusable mouthpiece intended for a similar or identical purpose.

Figure 14:
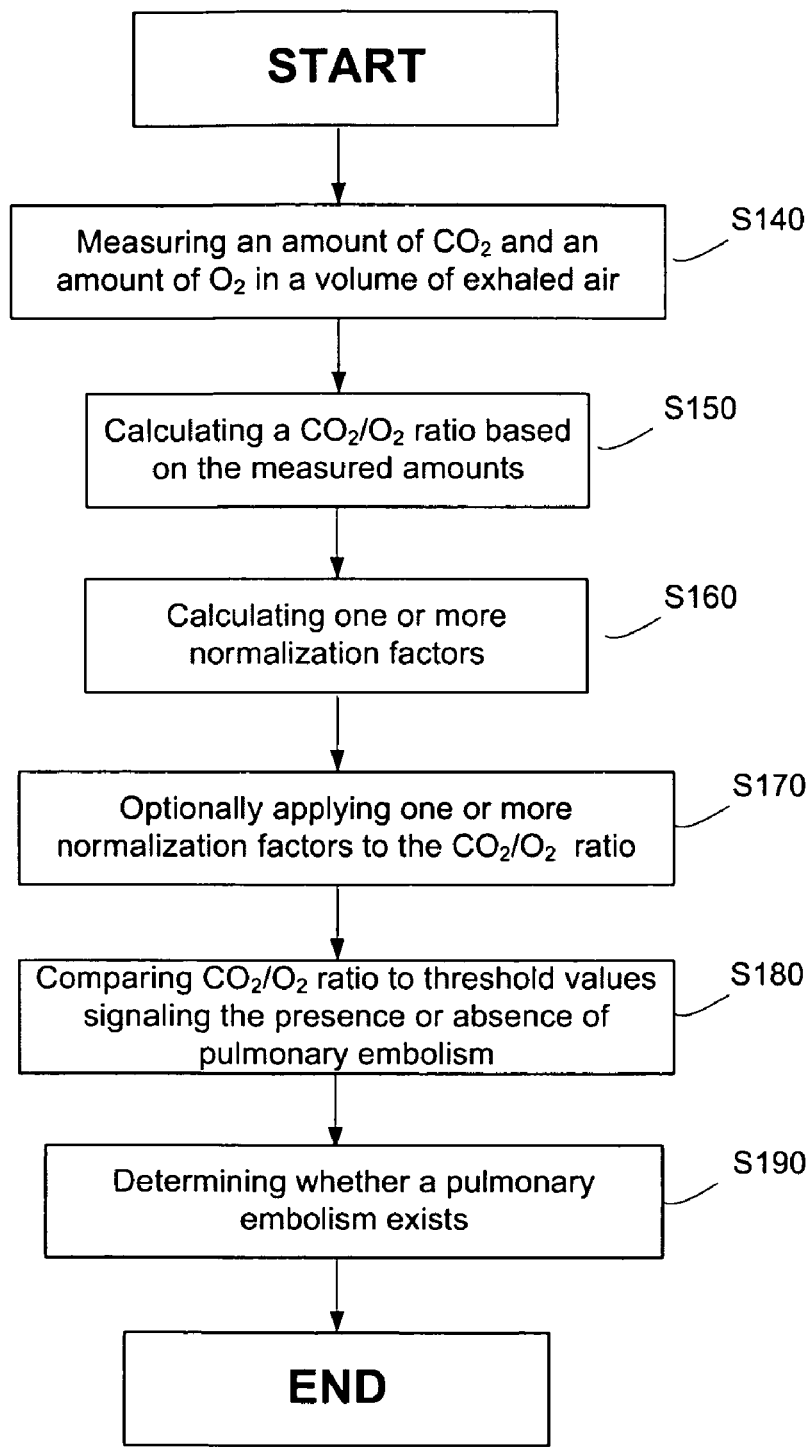
FIG. 14 is a flowchart of a one exemplary method of diagnosing respiratory dysfunction using the system of the present invention.
Figure 15:
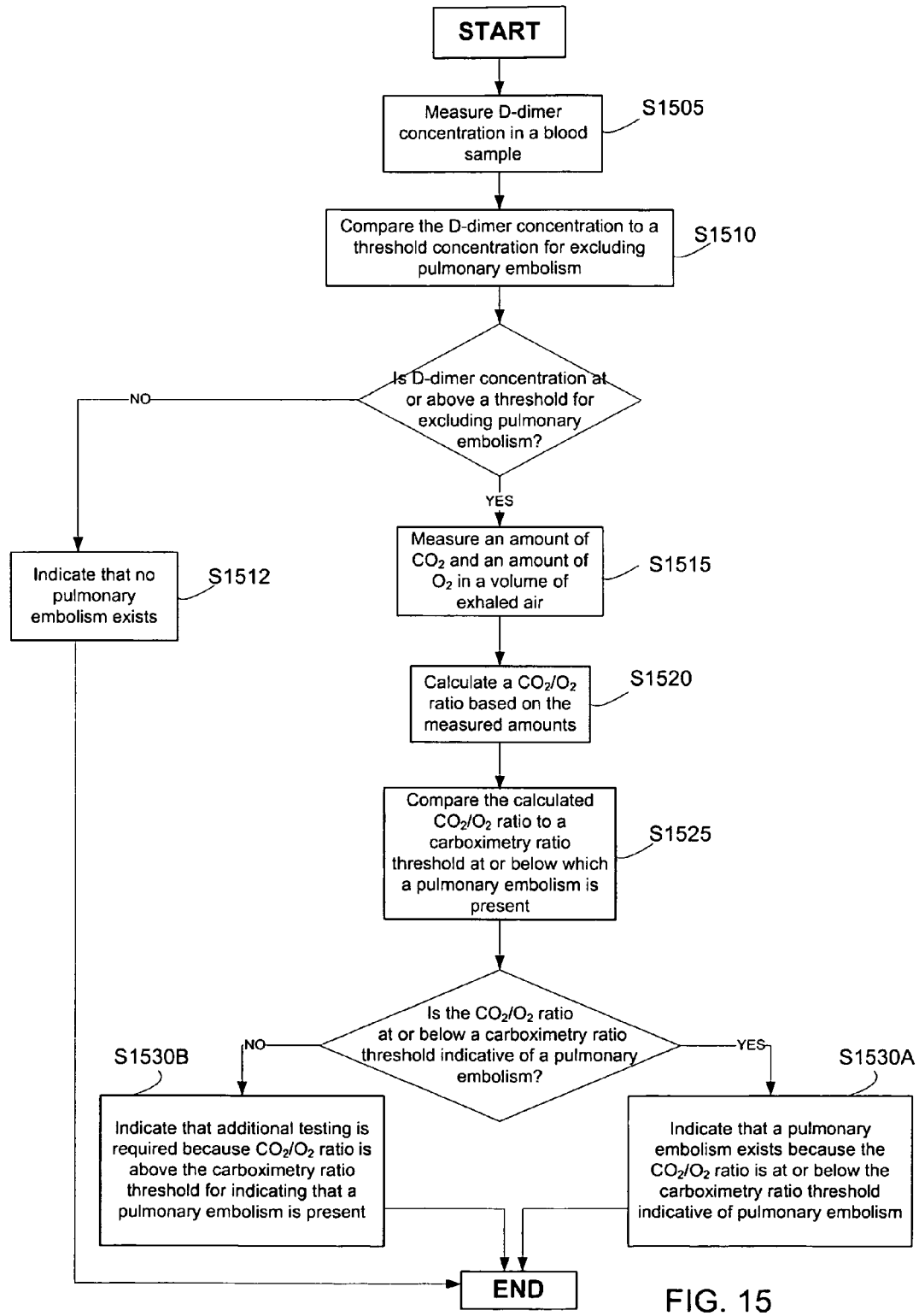
FIG. 15 is a flowchart of another exemplary method of diagnosing respiratory dysfunction using the system of the present invention.

Turning now to FIGS. 14 and 15, the present invention also includes methods for diagnosing a physiological abnormality and for particularly diagnosing a pulmonary embolism using the above-described system 10. Because gas exchange decreases when a pulmonary embolism blocks a pulmonary artery, the ratio of carbon dioxide to oxygen (carbox) in a volume of exhaled air also decreases. Referring to a first step S140 of the method of FIG. 14, the sensors of system 10 measure carbon dioxide and oxygen content of a volume of air flowing through the airway 30. The system measures concentrations of carbon dioxide and oxygen and derives partial pressure values from those measurements. In a second step S150, the system 10 calculates a carbox ratio and displays data relating to these measurements. The carbox ratio general represents a partial pressure calculation of carbon dioxide produced over a partial pressure calculation of unconsumed oxygen. Based on predetermined threshold values indicative of the presence or absence of a pulmonary embolism, the system 10 identifies whether measurements are determinative of respiratory dysfunction.

Additionally, as mentioned earlier, the system 10 includes a display 24 having menus and/or data representations not only related to carboximetry measurements but also related to a number of additional measurements, including for example a patient's heart rate, tidal volume, and dead space volume. Some of these additional measurements and calculations derived therefrom at a third step S160 enable a more accurate determination of the presence or absence of a pulmonary embolism. At a fourth step S170, the method involves applying these additional measurements to the carbox ratio thereby refining predictive accuracy of any carboximetry calculations falling near or between threshold values indicative of the presence or absence of a pulmonary embolism. These additional measurements and calculated factors, or normalization factors, work independently and in combination to increase the precision with which the system 10 determines whether a patient exhibits a pulmonary embolism.

Clinical studies of patients using the system 10 yield a cloud of data representing patients manifesting pulmonary embolisms, patients not manifesting pulmonary embolisms, and patients whose measurements are inconclusive. Applying normalization factors to this data pool better separates these measured data points into delineated groups falling on either side of a threshold value distinguishing patients with pulmonary embolisms from those without pulmonary embolisms. This increased delineation aids in diagnosing patients whose measurements are otherwise inconclusive.

Statistical data analyses are applicable to this delineation process, and these analyses may establish sensitivity, or true positive readings, at a certain percentage that also minimizes specificity, or the number of false positive readings. For example, this system 10 may successfully catch 95% of patients veritably experiencing pulmonary embolisms while identifying 95% of patients not manifesting pulmonary embolisms. These limits derive from thresholds determined during statistical analyses of clinical data, including comparing discreet values to values extrapolated from smooth Gaussian distributions. Establishing these percentages and extrapolating plotted study data identifies established threshold values by which to analyze real time clinical measurements.

Returning now to the method of FIG. 14, the fourth step S170 of the present method for diagnosing pulmonary embolisms recites employing normalization factors to measured data. A fifth step S180 recites comparing that normalized data to established threshold values determined though the above-described clinical studies and data analyses. A final step S190 involves diagnosing true instances of pulmonary embolism based on the comparison in step S180.

In one embodiment of the present method, measured dead space in a volume of exhaled air functions as a particularly effective normalization factor for refining the conclusiveness with which the ratio of carbon dioxide to oxygen indicates the presence of a pulmonary embolism. As is known in the art, the dead space volume refers to the portion of any tidal breath without gas exchange. Numerous methodologies known in the art are available for determining the dead space volume, including for example the Fletcher-Fowler method. The Fletcher-Fowler method includes measuring a carbon dioxide concentration across an exhalation period, resulting in a curve representing the exhaled volume as a function of carbon dioxide concentration. Integration of the curve about an equilibrium point results in the calculation of a dead space volume, which may or may not be indicative of a respiratory dysfunction such as pulmonary embolism.

Dead space alone functions effectively as a normalization factor for separating true positive readings indicative of the veritable presence of pulmonary embolism from false positive readings that falsely indicate the presence of pulmonary embolism. One way to apply the dead space normalization factor to the carboximetry ratio of carbon dioxide to oxygen in an exhaled volume of air is first to measure dead space over a collection of breaths and then calculate a median dead space value for that collection of breaths. Then, using measurements from a single breath, multiply the carbox ratio by a ratio of the expected dead space value to the median dead space value for the patient's collection of breaths. Expected dead space value may be a text book value for a certain population. Other factors may influence this determined value, such as a patient's history and metabolism. Comparing the resulting dead space normalized carbox value to a threshold value determined through clinical studies identifies carbox ratio values that otherwise falsely indicate the presence of pulmonary embolism. Alternatively, dead space may be used to qualify a single breath as usable for valid carboximetry calculations. For example, if exhaled volume exceeds 1.5 times the dead space volume, a breath may be valid for calculating a carbox ratio.

In an alternative embodiment, dead space functions as an effective normalization factor either in combination with or independently of additional normalization factors. One such factor that operates independently is respiratory quotient (RQ). Calculating RQ requires an additional measurement of the amount of oxygen consumed in a volume of inhaled air. Dividing this measured value of oxygen by the measured amount of carbon dioxide produced in a volume of exhaled air produces the RQ value. RQ is useful in normalizing readings based on what a patient is metabolizing, for example fats, carbohydrates and proteins. Applying RQ as a normalization factor helps sort patients whose metabolic changes may influence carboximetry readings and produce misleading results around and between threshold carbon dioxide to oxygen ratio values.

In yet another embodiment of the present method, applying minute volume calculations to dead space normalized caboximetry values further refines data analysis. Minute volume is a volume of inhaled air measured over a period of one minute, and this volume increases when a patient manifests a pulmonary embolism. High minute volumes, however, are particularly useful discriminators for identifying patients without pulmonary embolisms who nonetheless produce low carbox ratio values because they are hyperventilating. When applied to the dead space normalized carbox ratio as a normalization factor, minute volume identifies patients who merely are hyperventilating and producing carboximetry readings mimicking those indicative of pulmonary embolism. Negative pulmonary embolism readings for patients with low carbon dioxide to oxygen ratios falling below a threshold validly identify patients without pulmonary embolisms.

In an alternative embodiment of this method of diagnosing a pulmonary embolism using system 10, minute volume also functions an effective normalization factor when applied to the dead space normalized carbox ratio in conjunction with another normalization factor, uptake rate. Applying an uptake rate value to a minute volume measurement produces an improved gross indicator of hyperventilation. Uptake rate is the amount of oxygen absorbed by a patient's lung over a period of one minute. Oxygen levels in a breath of air decrease over a length of time that air remains in a patient's lungs. Because a pulmonary embolism blocks arterial flow, more oxygen remains in a volume of air exhaled by a patient manifesting a pulmonary embolism. By measuring oxygen levels over the duration of an exhaled breath, system 10 determines the rate at which oxygen levels decrease during that exhaled breath, and this rate is determinative of the rate with which a patient's lungs absorb oxygen. This rate of change is low for patients with pulmonary embolisms whose lungs are unable to absorb oxygen effectively. Calculating the ratio of minute volume to uptake rate produces a value indicative of ventilation rate to perfusion rate, and comparing that calculated value to a known threshold value identifies patients who are hyperventilating rather than manifesting respiratory dysfunction indicative of pulmonary embolism.

In yet another alternative embodiment, applying alveolar minute volume to the carbox ratio produces useful normalized values. Alveolar minute volume is measured minute volume less calculated dead space. This derived normalization factor further refines the determinative value of a carbon dioxide to oxygen ratio to diagnose a pulmonary embolism.

Phase 2 slope normalization provides yet another alternative method for diagnosing pulmonary embolism using data collected by the system 10. The system 10 measures carbon dioxide and oxygen content in a volume of exhaled air. During the duration of a single exhalation, the ratio of these measurements varies sharply at an identifiable point of change when the rate of molecular exchange varies sharply. Phase 2 slope normalization entails identifying this point of change that leads into a second slope phase, the phase 2 slope, and calculating the carbox ratio at this point of change. System 10 then diagnoses pulmonary embolism by further applying the above-described normalization methods to this phase 2 slope ratio.

In another embodiment, the method of diagnosing pulmonary embolism comprises calculating an expected ratio of carbon dioxide to oxygen and comparing this value to actual measured ratios of carbon dioxide to oxygen. In this alternative method, the system 10 displays actual and expected carbox ratios for analysis by a clinician. Calculating an expected ratio depends on a number of physiological factors, such as height, weight, gender, and age. The system 10 calculates an expected carbox ratio based on a clinician's inputting these patient-specific factors. The clinician then determines whether a patient's exhaled air measurements divert from expected ratios and thereby indicate the presence of respiratory dysfunction. Additionally, this comparison of measured data to expected data may be useful in conjunction with data analyses using methods for diagnosing respiratory dysfunction that involve normalization factors.

In another alternative embodiment, plethsmograph measurements aid in diagnosing pulmonary embolisms using dead space normalized ratios of carbon dioxide to oxygen in a volume of exhaled air. Plethsmographs measure variation in a patient's heartbeat between an inhale portion of a breath and an exhale portion of that breath. Generally, breathing alters chest cavity pressure and effects rhythmic beating of a heart. Patients experiencing pulmonary embolisms exhibit an altered pressure regulation of their hearts wherein their heartbeats respond less to deviations in chest cavity pressure between each inhalation and exhalation. In other words, because patients with pulmonary embolism have already-pressurized hearts, they also have a more consistent heartbeat between inhalation and exhalation than healthy individuals.

Applying plethsmograph readings to normalized ratios determined by the system 10 operating simultaneously with the plethsmograph improves specificity by conclusively identifying patients without pulmonary embolisms who nonetheless exhibit low dead space normalized carbon dioxide to oxygen ratios. This method uses plethsmograph readings to calculate a heart period ratio of mean exhale period to mean inhale heart period. Comparing this value and/or inhalation and exhalation heart period measurement variability values to known threshold values then identifies patients without pulmonary embolisms who exhibit low dead space normalized carbox ratios.

Although normalization factors are useful in determining the presence of pulmonary embolism, other methods of determination also exist. For example, combining a blood based measurement such as D-dimer with an end-tidal carboximetry measurement can provide a non-invasive, rapid, and reliable bedside method to screen for pulmonary embolism. Turning now to FIG. 15, the present invention includes a method for determining the presence of a pulmonary embolism comprising combining a D-dimer measurement with a carboximetry measurement to determine the presence or absence of pulmonary embolism.

In one embodiment, a first step S1505 and second step S1510 respectively comprise analyzing a blood sample for D-dimer concentration and comparing the D-dimer concentration to a threshold value for indicating a potential presence of pulmonary embolism. D-dimer concentration is a reliable negative predictor for pulmonary embolism. If the D-dimer concentration falls below a threshold value, that result is conclusive evidence that pulmonary embolism fails to exist. A D-dimer concentration falling at or above the threshold for a negative pulmonary embolism result, however, provides no absolute evidence of pulmonary embolism, and determining a positive result requires additional testing. If the D-dimer concentration falls below a threshold indicative of concern, a third step S1512 indicates that no pulmonary embolism exists and that no further testing is required. If the D-dimer concentration falls at or above the threshold indicative of concern, additional testing is required to determine whether a pulmonary embolism is present.

Figure 28:
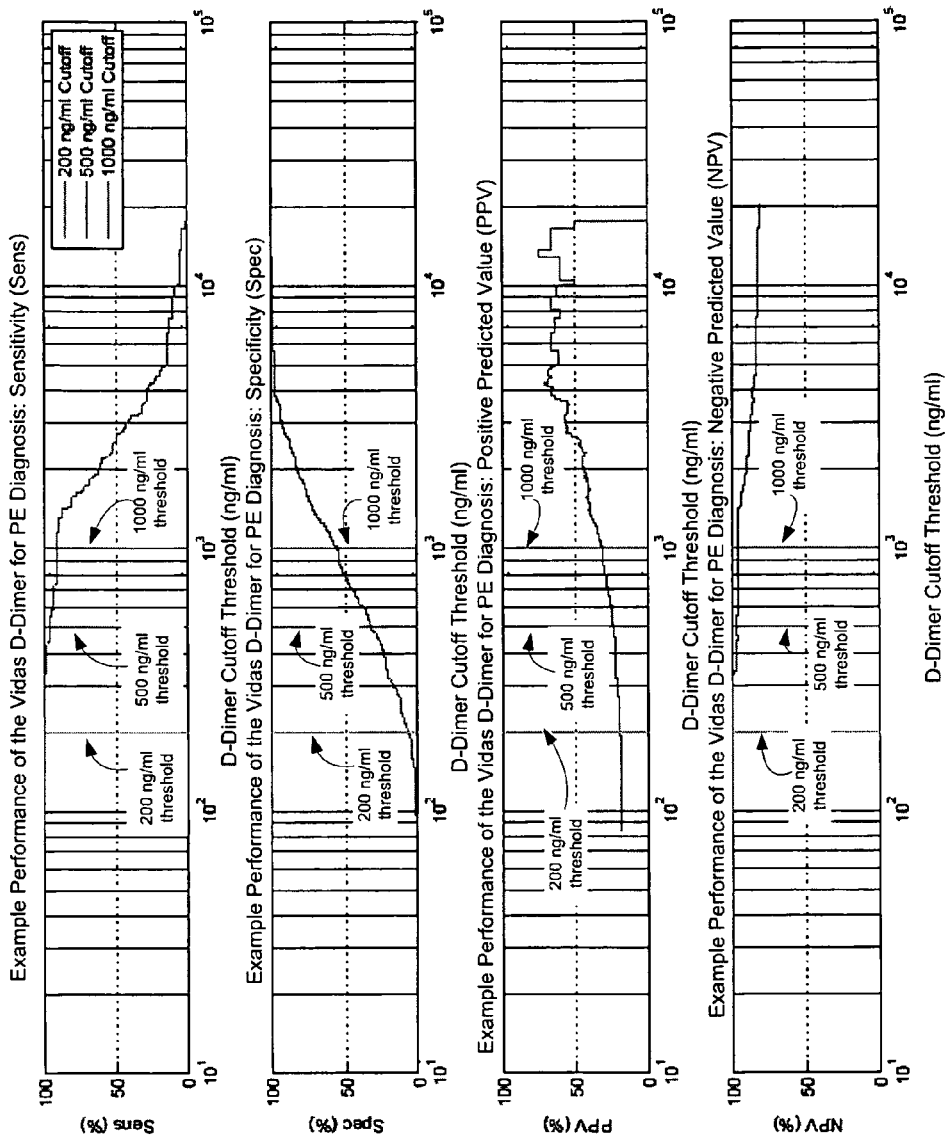
FIG. 28 depicts individual plots showing D-dimer sensitivity, specificity, positive predicted value and negative predicted value as a function of the D-dimer cut-off threshold.
Figure 29:
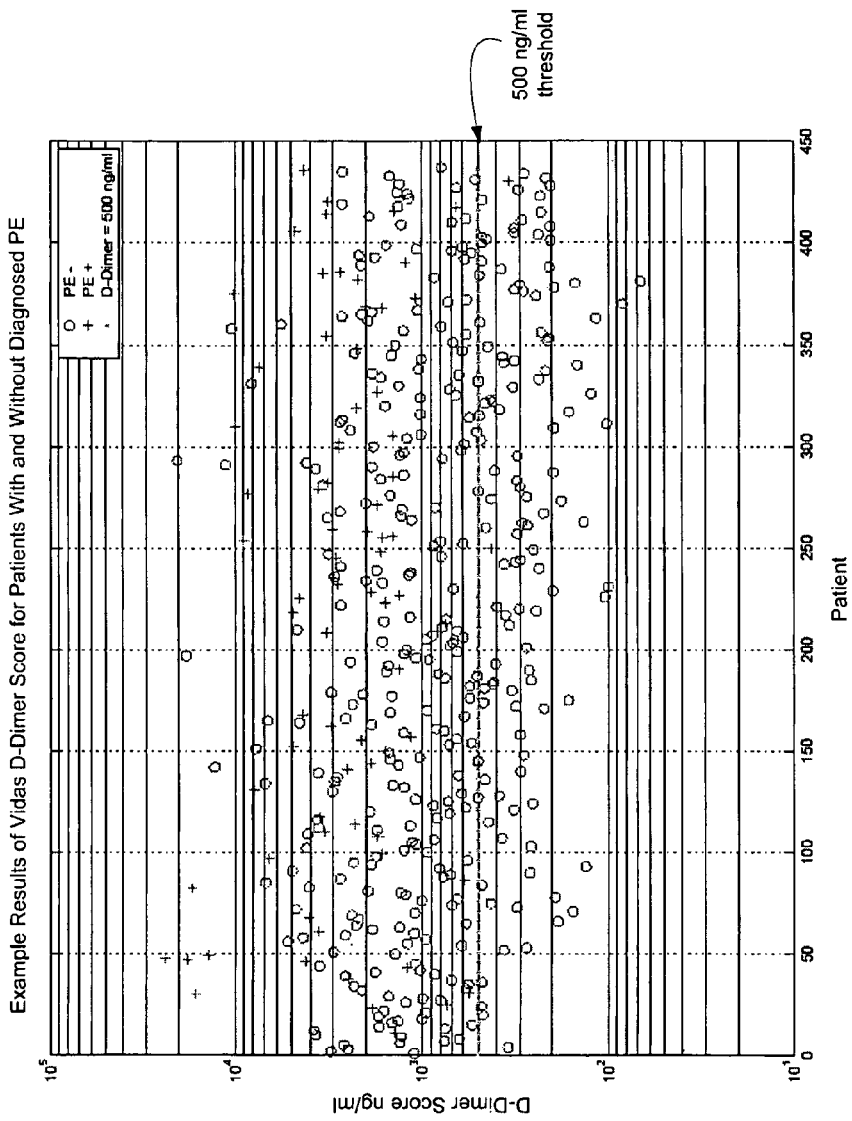
FIG. 29 is a scatter plot of D-dimer scores for 437 patients.
Figure 30:
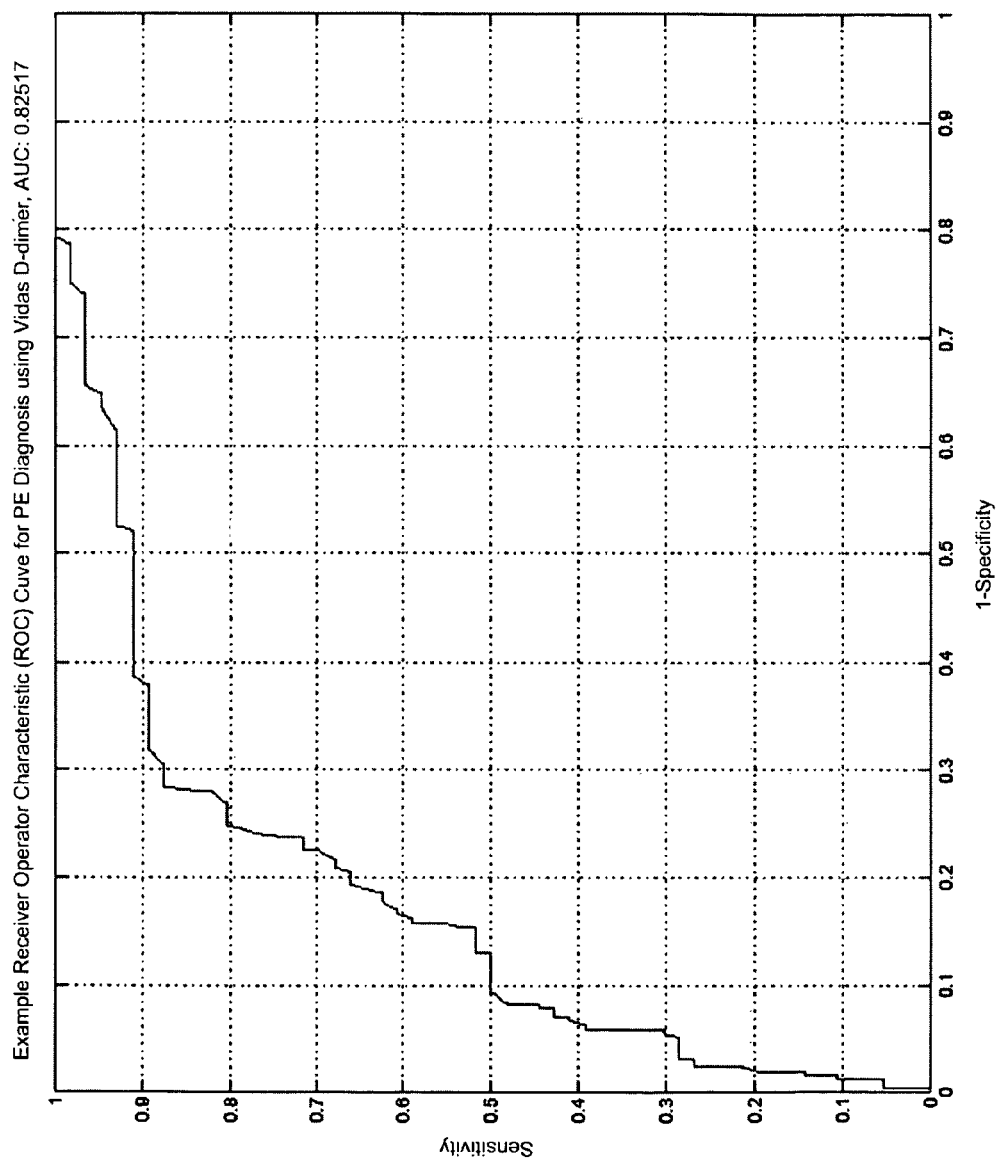
FIG. 30 is a receiver operating curve based on the data of FIG. 29 and illustrating diagnostic performance of a D-Dimer test device as the D-dimer cutoff threshold is adjusted.

A suitable threshold value for this purpose is a D-dimer concentration falling in a range of 100 to 2000 nanograms per milliliter (ng/ml), and more particularly 500-1000 ng/ml. In one embodiment the threshold value equals the VIDAS® D-dimer value of 500 ng/ml or thereabout. FIGS. 28 through 30 demonstrate these ranges applied during a clinical trial of 437 patients. FIG. 28 depicts four individual plots showing D-dimer sensitivity, specificity, positive predicted value and negative predicted value as a function of the D-dimer threshold value. Three example thresholds, 200 ng/ml, 500 ng/ml, and 1000 ng/ml, are shown on each plot: to provide a graphical indication of how each performance metric is affected as the cutoff threshold is changed. FIG. 29 depicts a scatter plot of D-dimer scores for 437 patients, and the 500 mg/ml D-dimer threshold value is indicated. Patients above this line were diagnosed as having pulmonary embolism based on the D-dimer test alone. This group represents the patient population requiring carboximetry screening, using a device such as the system 10 disclosed herein, for example. Patients below the 500 ng/ml threshold value line were diagnosed as having no pulmonary embolism and therefore requiring no additional testing. FIG. 30 depicts an example receiver operating curve for the data set of FIG. 29. This is a standard chart used to relate the diagnostic Specificity and Sensitivity performance of a device. An area under the curve of 1 would be a perfect diagnostic. Here, the area under the curve (AUC) is 0.82517. The area under the curve of this chart and the shape of the curve illustrate the diagnostic performance as the D-dimer cutoff threshold is adjusted.

In an exemplary embodiment of the present invention, one such method of additional testing comprises a fourth step S1515 and a fifth step S1520 respectively directed toward measuring a concentration of carbon dioxide and a concentration of oxygen in a volume of exhaled air and directed toward calculating a carboximetry ratio based on the measured values. The exemplary system 10 and exemplary methods described above with regard to the system 10 are suitable for performing the fourth step S1515 and the fifth step S1520 of the present analytical method.

To evaluate a patient further for the presence of pulmonary embolism, a sixth step S1525 comprises comparing a carboximetry ratio to a threshold value that indicates the presence of a pulmonary embolism. For example, such a value may be between 0.25 and 0.30, and preferably may be 0.28 or thereabout, as presented in U.S. Pat. No. 6,575,918, herein incorporated by reference. The method thus comprises determining whether a pulmonary embolism exists or whether a patient requires additional testing. In cases when the calculated carbox ratio is less than or equal to the carbox ratio threshold, a pulmonary embolism likely is present, and the method comprises a seventh step S1530A of indicating the presence of a pulmonary embolism. For example, in one embodiment, if the carboximetry ratio indicates the presence of pulmonary embolism, the control unit 20 of the exemplary system 10 described above may instruct an operator to treat the patient for pulmonary embolism. If the carbox ratio is greater than the threshold value, thereby indicating that a pulmonary embolism likely is not present, then an alternate seventh step S1530B comprises indicating that additional testing is required. For example, in one embodiment, the control unit 20 described above may instruct an operator to conduct further testing. In summary, a positive D-dimer test result and positive carboximtery test result therefore together indicate the presence of pulmonary embolism, and a positive D-dimer test result combined with a negative carboximetry test result indicates a need for additional testing.

In another embodiment of the method, the D-dimer and Carboximetery test steps may be performed simultaneously or in reverse order. Because these two tests are independent of one another, the particular order of testing could be reversed or data could be collected simultaneously and compared to threshold values simultaneously. Furthermore, adjusting the D-dimer threshold value and carboximetry ratio threshold value within the disclosed ranges may limit the number of falsely identified pulmonary embolisms. Clinicians may elect to adjust these thresholds based on historical data collected with a particular D-dimer and/or carboximetery measurement device.

Exemplification of Normalization

Purpose of normalization

The carbox value, the partial pressure of carbon dioxide divided by the partial pressure of oxygen in an exhaled breath, is a metric with value in diagnosing pulmonary embolism. Comparing a patient's carbox value to threshold values determines whether the patient almost certainly has a pulmonary embolism, whether the patient almost certainly does not have a pulmonary embolism, or whether the results are inconclusive and that the patient requires further testing. The thresholds are determinable through clinical testing, which testing also determines the distribution of carbox values in a patient population.

The quantities making up the carbox value are partial pressure of oxygen and partial pressure of carbon dioxide in an exhaled breath. These quantities vary with other physiological parameters. Additionally, other measurable physiological parameters are affected by the presence of a pulmonary embolism. Normalization measures these other physiological parameters and combines them mathematically with the carbox value. This process compensates for the confusing effects of other parameters that may obscure the carbox value's diagnostic utility by combining the predictive value of a parameter with the carbox value to strengthen the data's diagnostic utility.

Data Used to Evaluate Normalization Techniques

These normalization techniques were evaluated in a 92 patient study using an Alpha Prototype 1 of the system 10. The study determined carbox values for a population with a clinical suspicion of pulmonary embolism and a baseline risk for elevated D-dimer. Twenty patients in the study were considered to have a pulmonary embolism.

Process for Evaluating the Data

A. Data Available

Each patient in the study produced data collected over approximately four periods of tidal breathing followed by a deep inhalation and exhalation. The data collected during this time included partial pressure of oxygen, partial pressure of carbon dioxide, air flow (L/s), and a plethsmographic signal.

B. Data Reduction

Data evaluation transpired in the following sequence of steps: A first step involved determining when each patient was inhaling and exhaling. A second step involved determining when distinct exhalations occurred for each patient's measurements. An exhalation occurred when the volume of air produced exceeded 0.1 L and when the length of exhale was at least one second. With exhalations identified, a third step included determining the dead space volume for each patient. The dead space for each breath was determined using the above-described Fletcher-Fowler method. The median dead space volume for the collection period was used as a patient's dead space measurement. Lastly, a fourth step involved determining representative carbox values for the patient. The breaths during which the exhaled volume exceeded the dead space volume while measuring less than 1.7 L determined a representative carbox value. In addition to the volume requirement for determining representative breaths, the carbon dioxide level and the oxygen level of these representative breaths changed by at least 5 torr.

For all qualifying breaths, a linear fit was made to the carbon dioxide versus volume curve and to the oxygen versus volume curve. The linear fit was an asymptotic line drawn at a point on the curve located between the knee, of each partial pressure versus volume curve and a 1 L measurement on the volume axis. In this study, when the exhaled volume exceeded 1.5 times the dead space volume, 1.5 times the dead space volume represented the knee of each curve. When the exhaled volume did not exceed 1.5 times the dead space volume, then the halfway point between the dead space volume and the maximum exhaled volume represented the knee of each curve. With asymptotic linear fits placed on each partial pressure versus volume curve, the data reduction then involved identifying the partial pressures of carbon dioxide and oxygen at the point where each respective linear fit reached either 1 L or the maximum exhaled volume, whichever was a smaller value. The data reduction then included dividing the extrapolated carbon dioxide value by the extrapolated oxygen value to calculate a carbox value for each representative breath. The median carbox value for all of a patient's breaths then represented the patient's carbox value.

Several other choices were available for determining the patient's carbox value. The fit could have had the form of a linear portion combined with an exponential portion. Although this study used 1.5 times dead space volume, the evaluation volume could have been a different value. The requirements for a legitimate breath could have been another value. Other methods of extracting a representative carbon dioxide and oxygen value could have worked as well. The particular method used for this study, however, was simple and effective. Additionally, for the data used in this study, no appreciable differences resulted from the style of fit selected or from the point at which oxygen and carbon dioxide values were determined from their representative curves.

C. Evaluating Normalization Effectiveness

1. Determining the Normalization Factor

Figure 16:
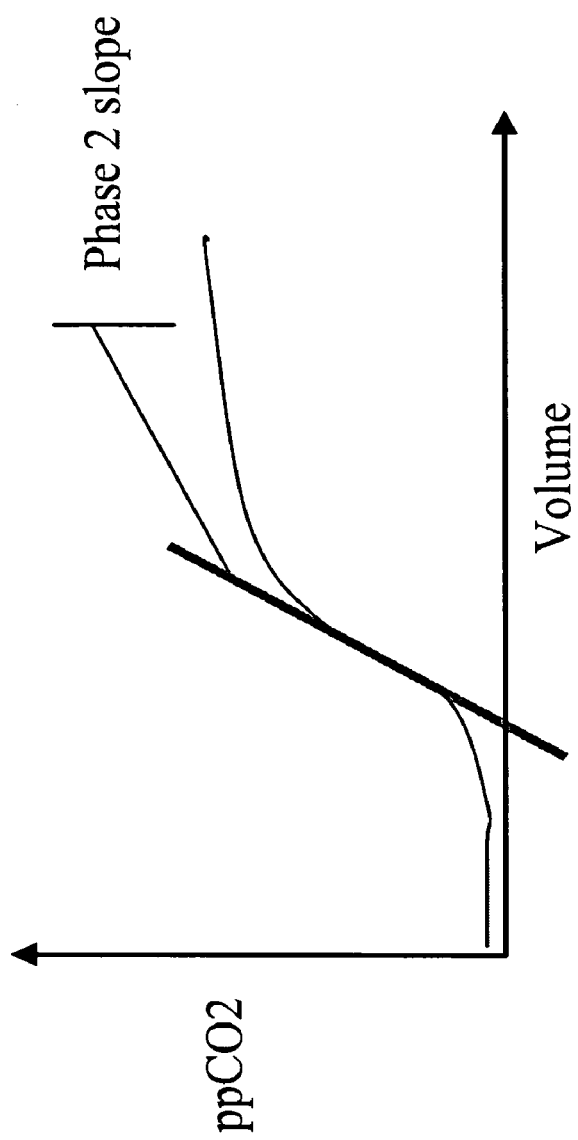
FIG. 16 is a depiction of identifying a phase 2 slope on a carbon dioxide versus volume curve.
Figure 17:
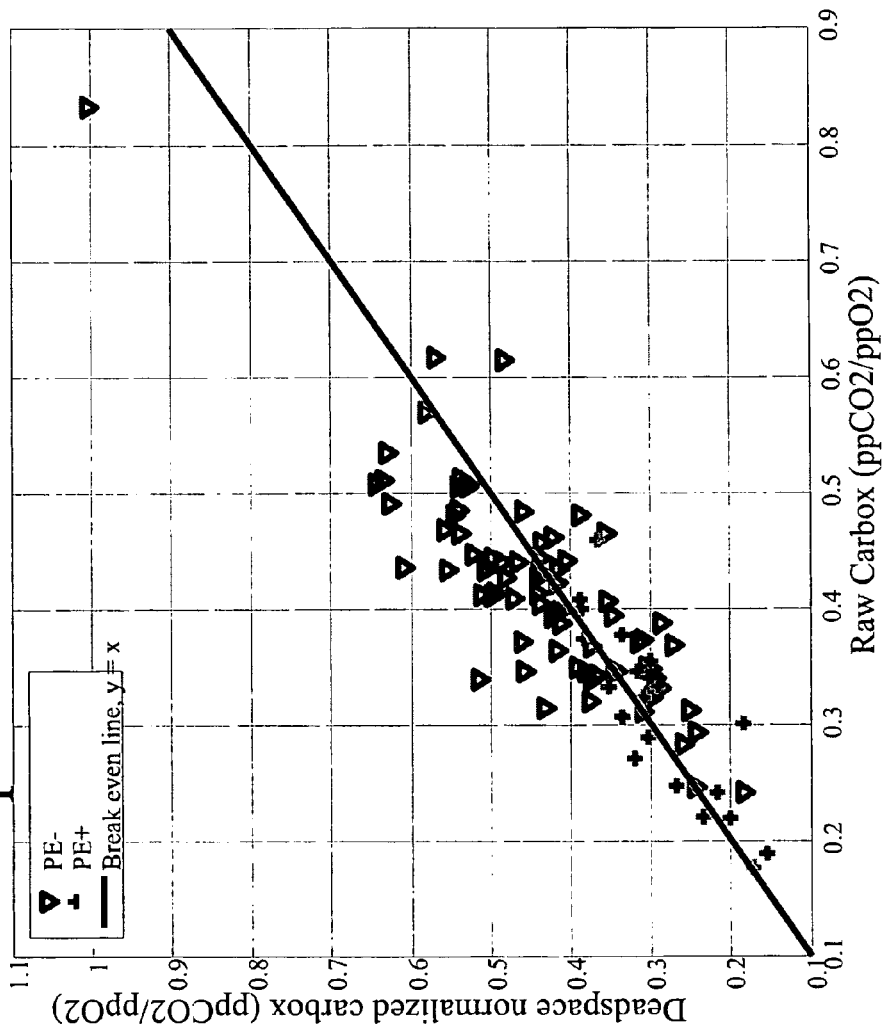
FIG. 17 is a scatter plot of clinical study data representing dead space normalized carbox ratios plotted against raw carbox ratios for patients with pulmonary embolisms and patients without pulmonary embolisms.
Figure 18:
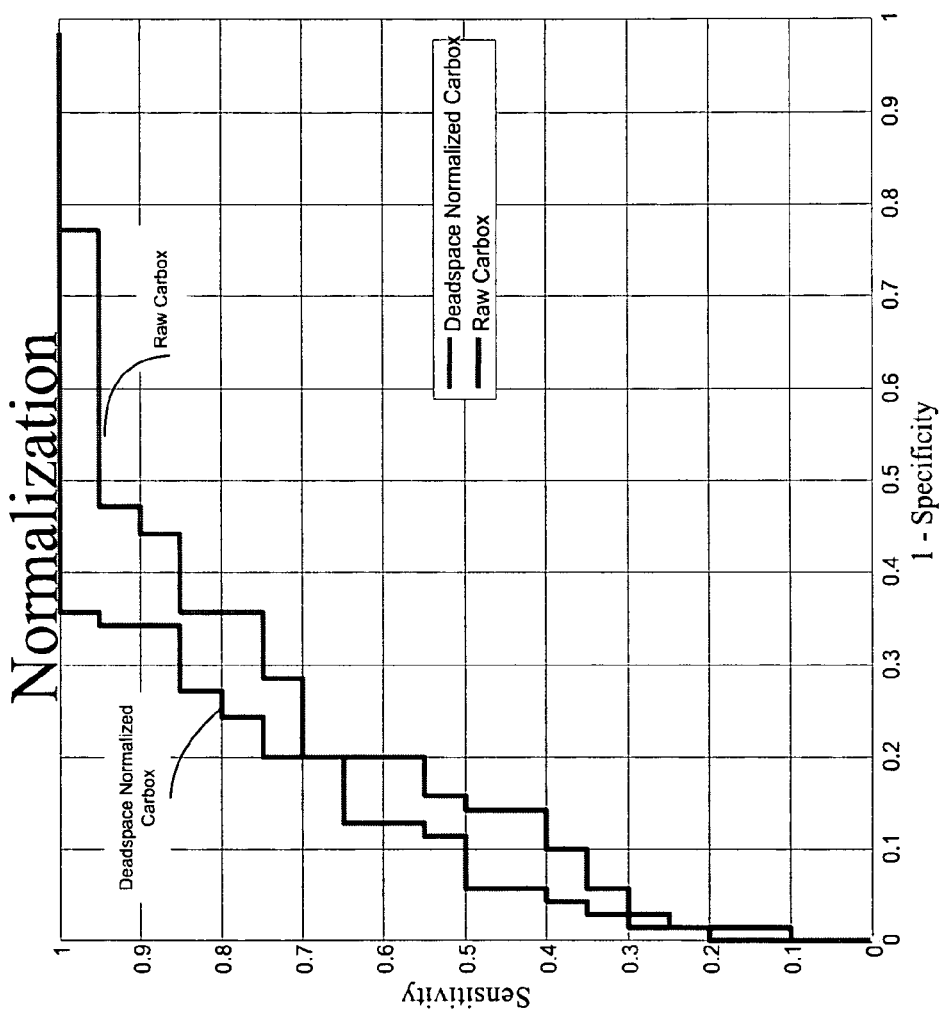
FIG. 18 is a Spec95 receiver operator curve for dead space normalized carbox ratios.
Figure 19:
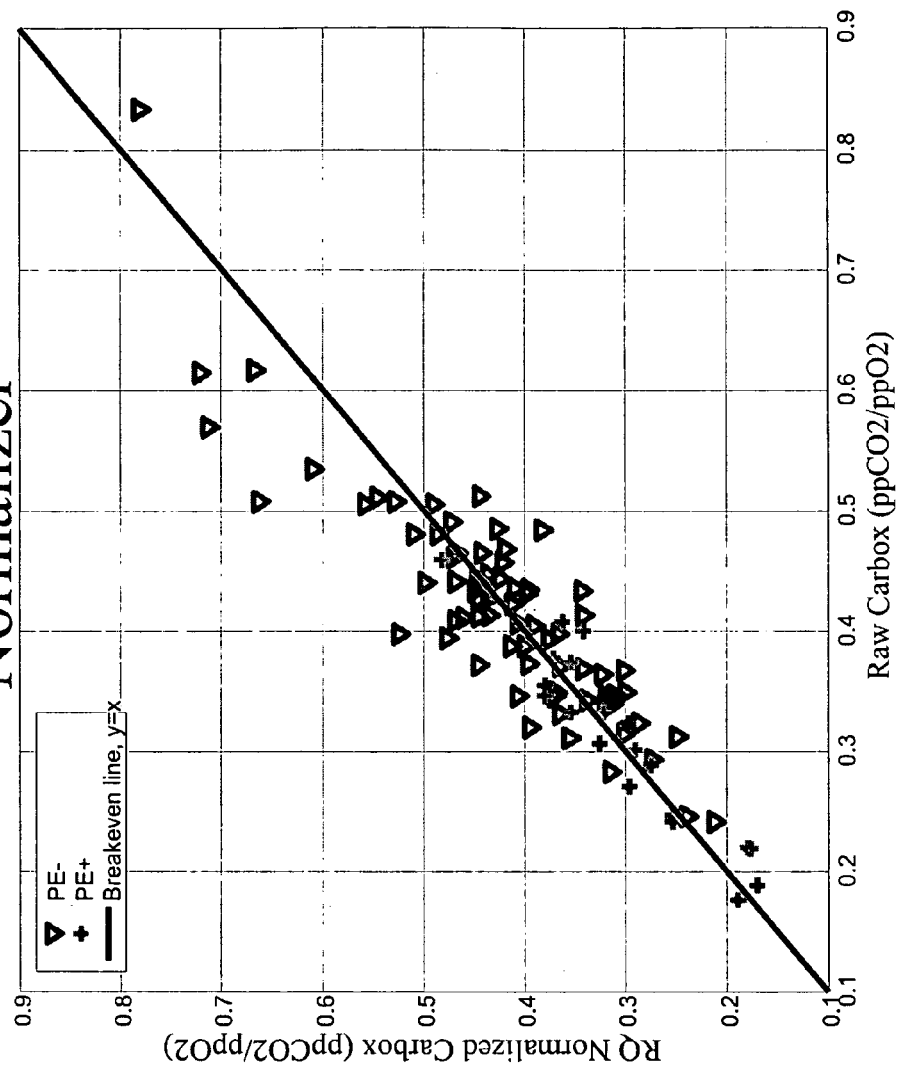
FIG. 19 is a scatter plot of clinical study data representing respiratory quotient normalized carbox ratios plotted against raw carbox ratios for patients with pulmonary embolisms and patients without pulmonary embolisms.
Figure 20:
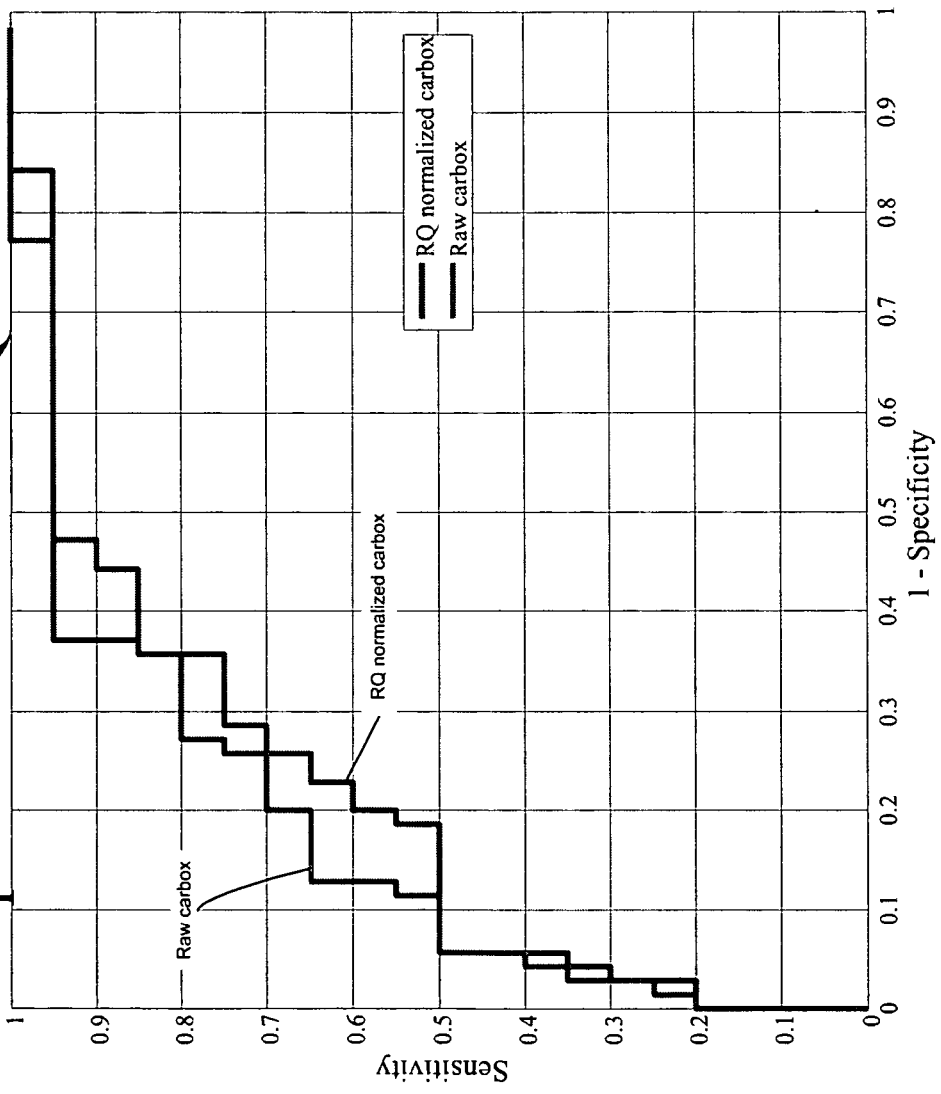
FIG. 20 is a Spec95 receiver operator curve for respiratory quotient normalized carbox ratios.
Figure 21:
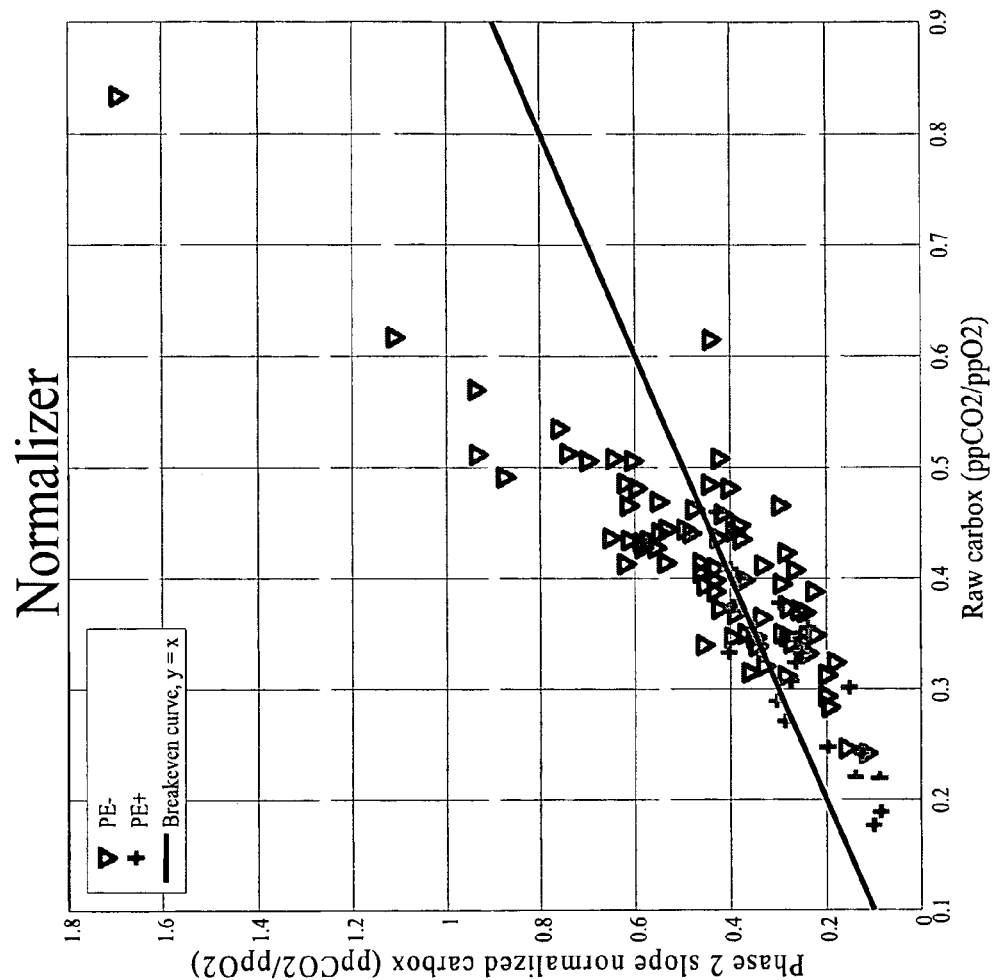
FIG. 21 is a scatter plot of clinical study data representing phase 2 slope normalized carbox ratios plotted against raw carbox ratios for patients with pulmonary embolisms and patients without pulmonary embolisms.
Figure 22:
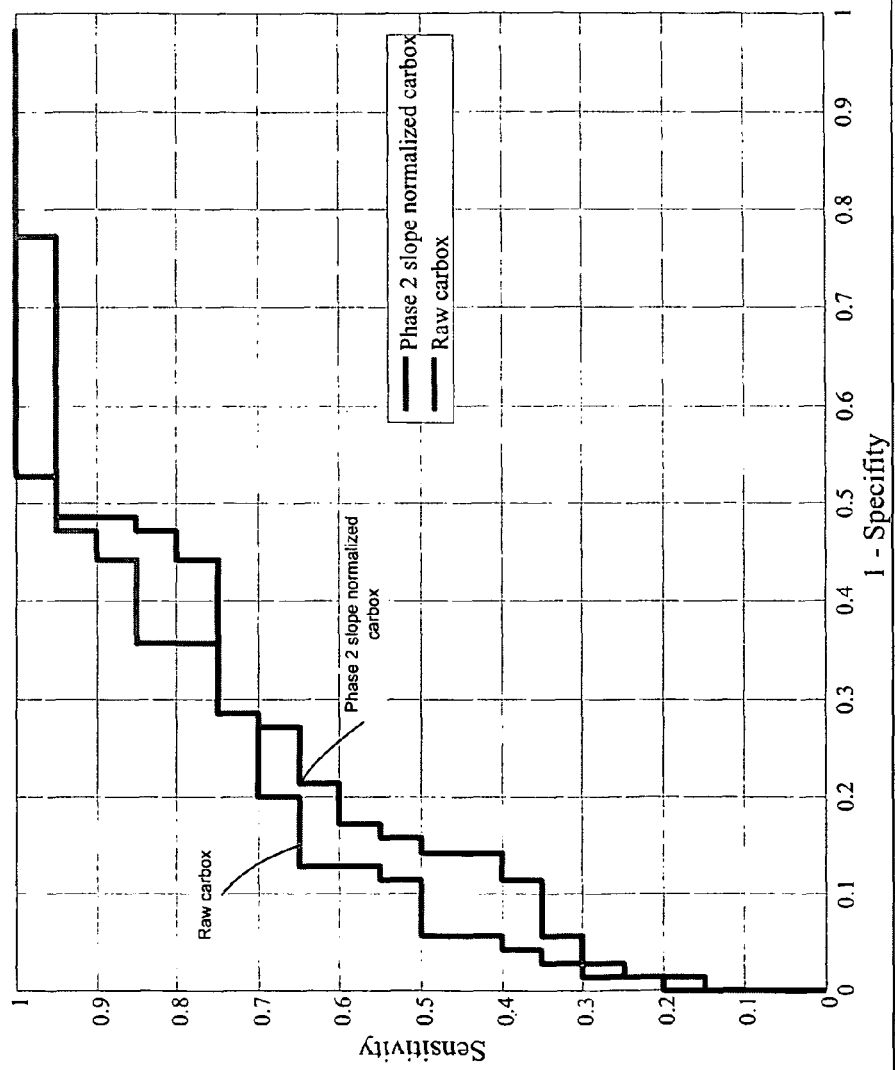
FIG. 22 is a Spec95 receiver operator curve for phase 2 slope normalized carbox ratios.
Figure 23:
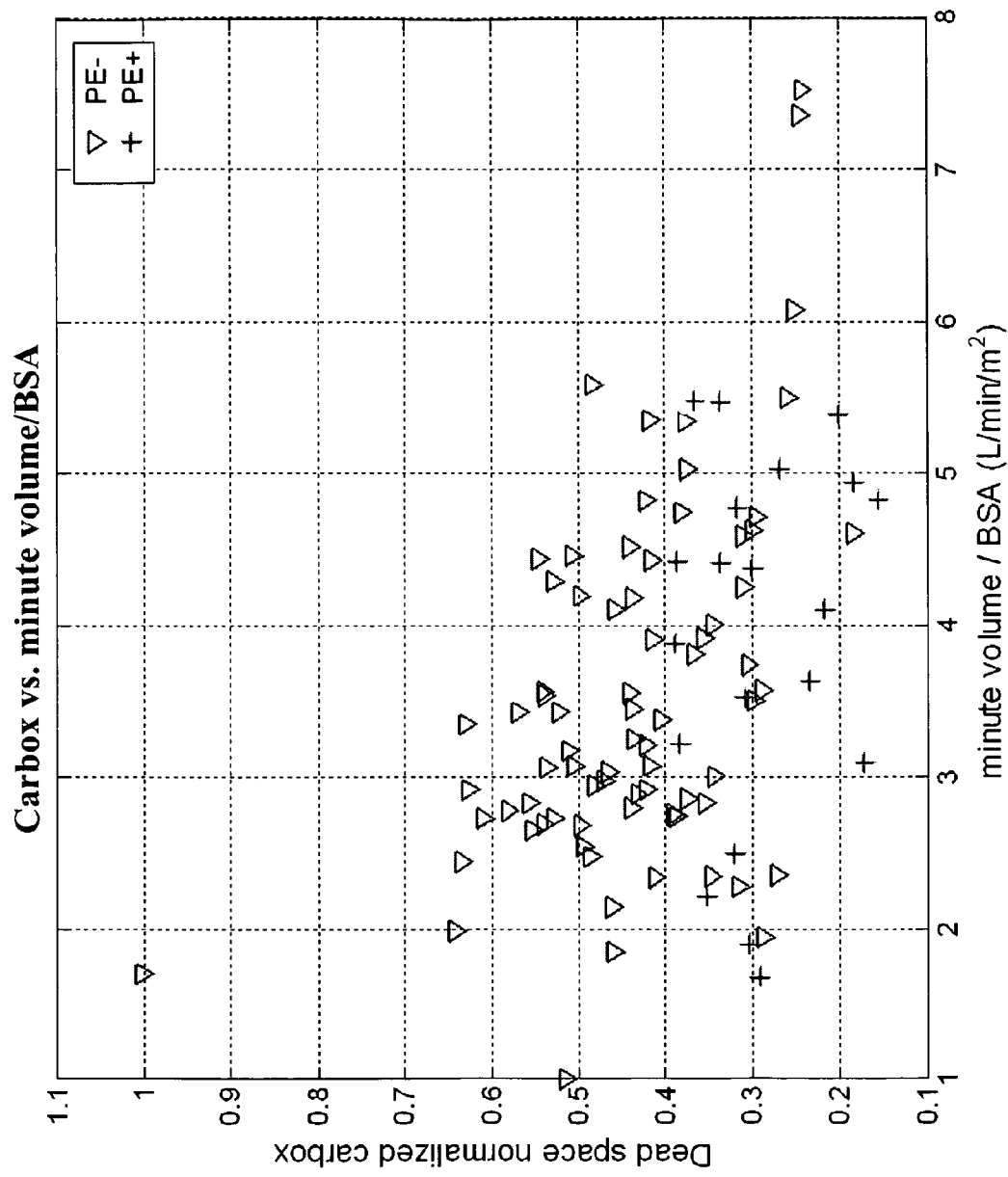
FIG. 23 is a scatter plot of clinical study data representing dead space normalized carbox ratios plotted against minute volumes for patients with pulmonary embolisms and patients without pulmonary embolisms.
Figure 24:
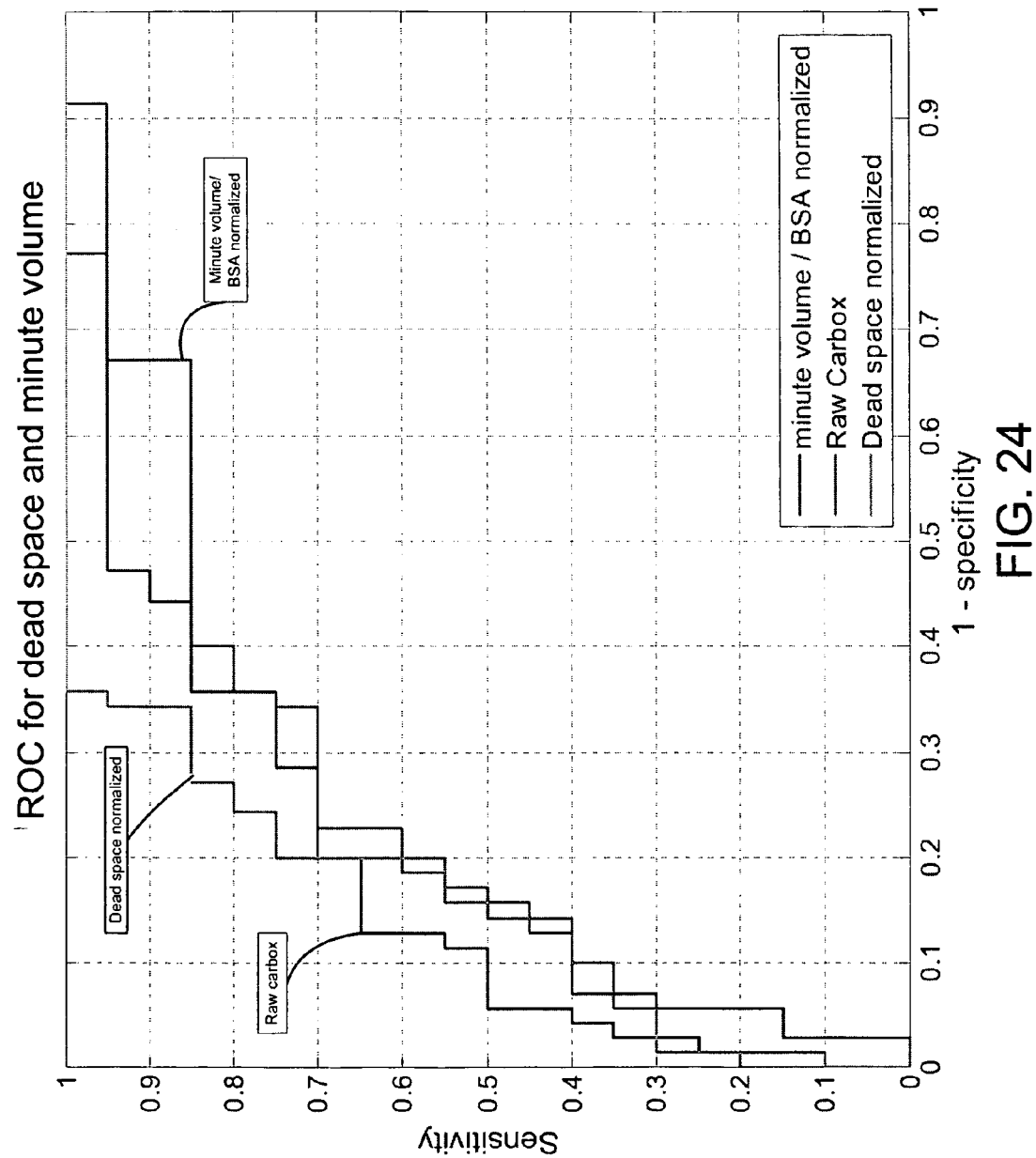
FIG. 24 is a Spec95 receiver operator curve for dead space and minute volume normalized carbox ratios.
Figure 25:
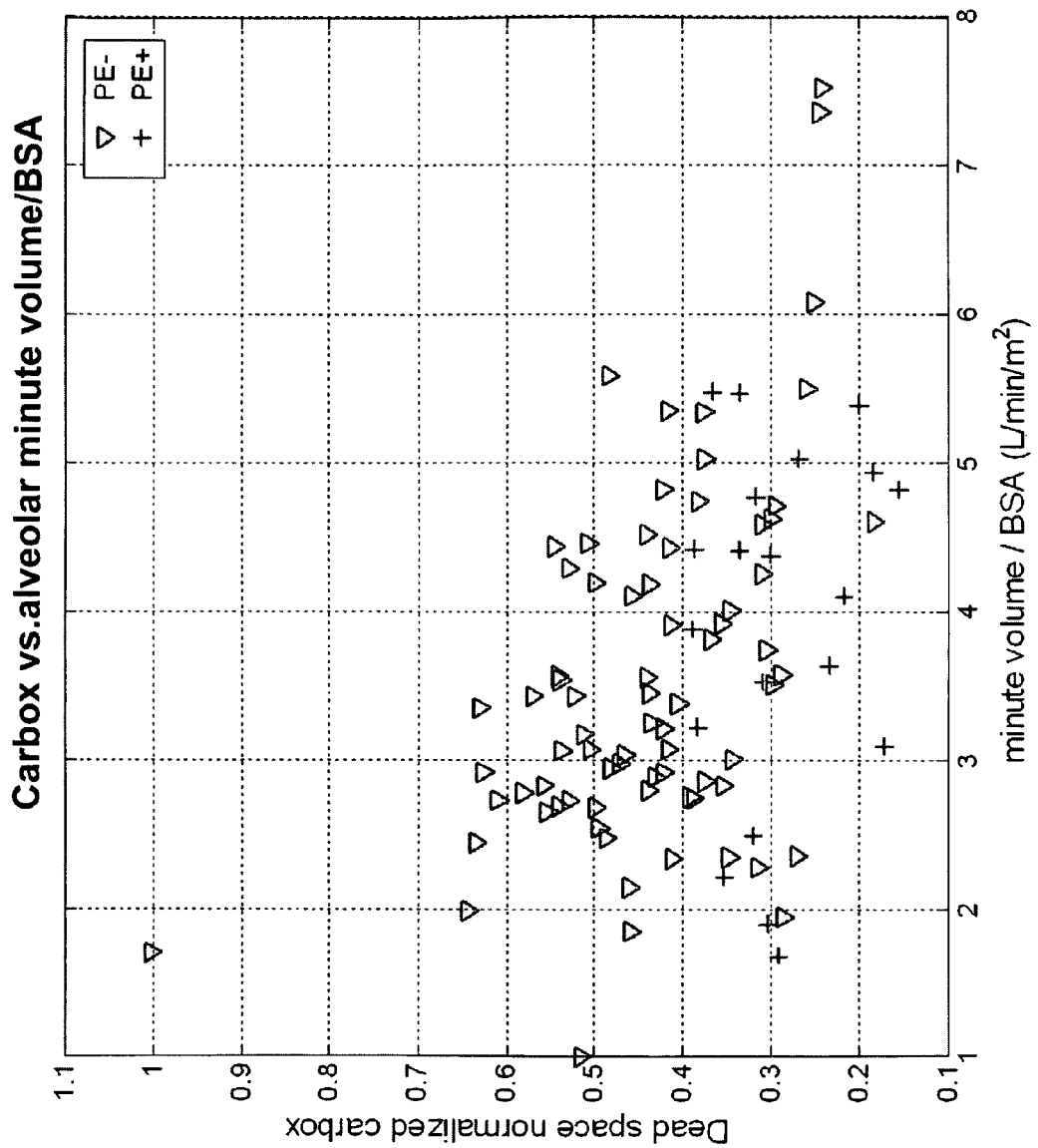
FIG. 25 is a scatter plot of clinical study data representing dead space normalized carbox ratios plotted against alveolar minute volumes for patients with pulmonary embolisms and patients without pulmonary embolisms.
Figure 26:
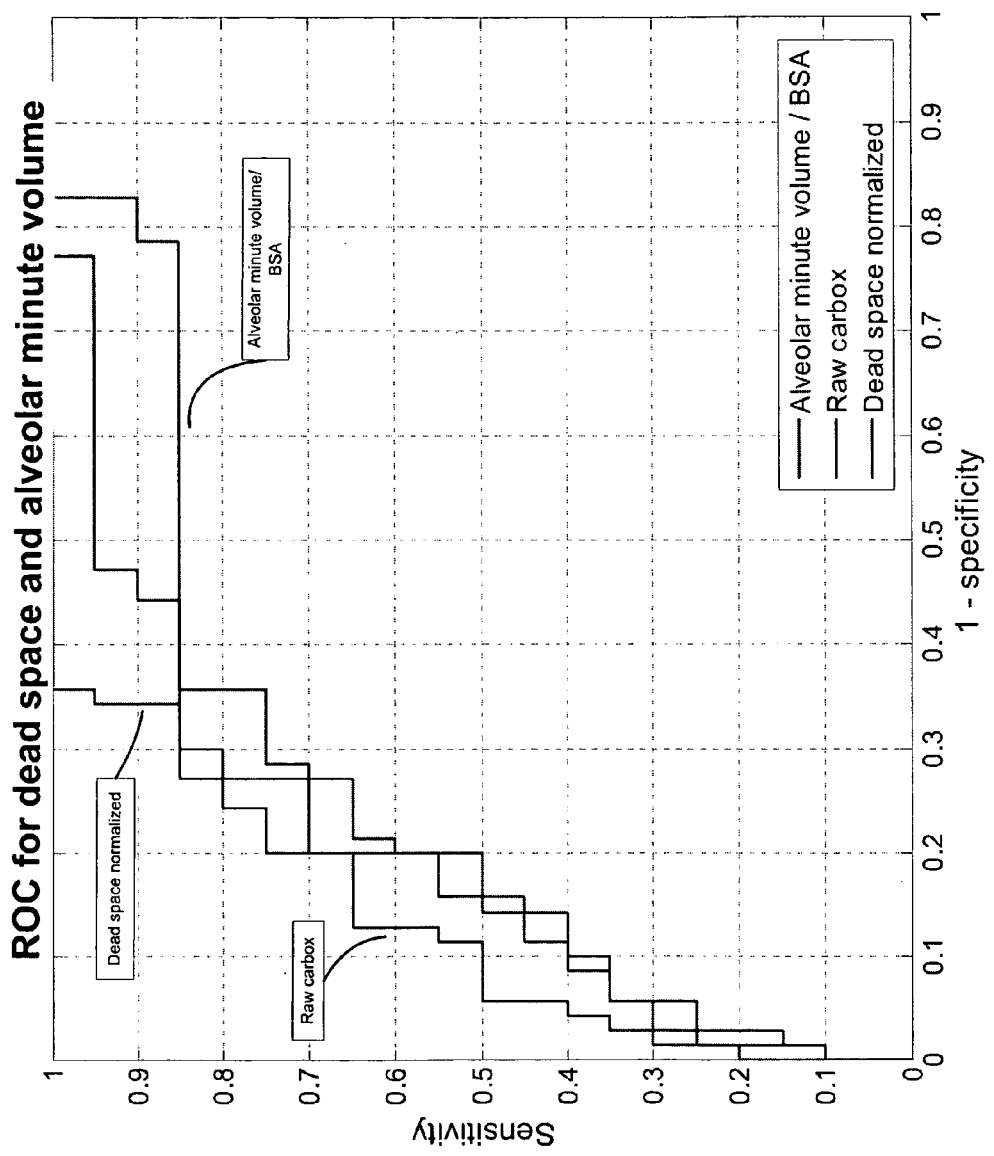
FIG. 26 is a Spec95 receiver operator curve for dead space and alveolar minute volume normalized carbox ratios.
Figure 27:
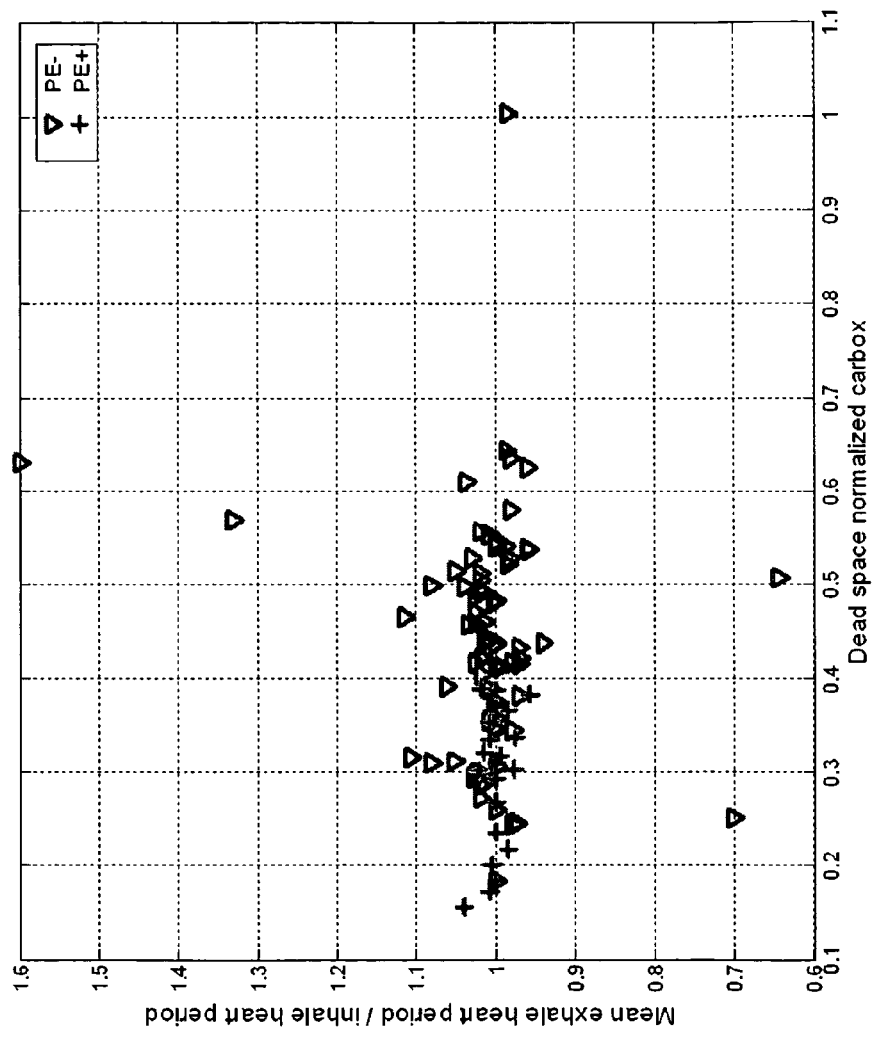
FIG. 27 is a scatter plot of mean ratios of exhale heart period to inhale heart period plotted against dead space normalized carbox ratios for patients with pulmonary embolisms and patients without pulmonary embolisms.

Next, the clinical study involved identifying the above-described normalization factors such as a patient's dead space, respiratory quotient (RQ), phase 2 slope, uptake rate and minute volume. The dead space-normalization factor represents the patient's dead space volume as already described. The respiratory quotient is defined as a ratio of oxygen consumed to carbon dioxide produced by a patient. In this study, RQ value was determined by integrating the change in oxygen and the change in carbon dioxide for all a patient's valid breaths. The phase 2 slope is defined as the maximum slope measured in the carbon dioxide versus volume curve. The depiction in FIG. 16 elucidates this point. In the study, the phase 2 slope determination involved fitting 100 lines to the carbon dioxide versus volume curve over 0.02 L sections of each breath and determining a maximum slope from this set of linear fits. A patient's phase 2 slope then represented a median value of all the maximum slopes determined for breaths considered valid for the purpose of evaluation.

2. Applying the Normalization Factors

The clinical study's data analysis then involved normalizing each patient's carboximeter value by various normalization factors. Dead space normalization involved dividing that carbox ratio by a patient's dead space value. Similarly, when normalizing using RQ, the study involved dividing patient's carbox value by their RQ value. The patient's phase 2 slope was multiplied by the carbox value to normalize carbox by this parameter. In all cases, the data analysis involved applying the mean value of each normalization parameter for all patients in the study in an opposite fashion to the application of the normalization factor. For example, the data analysis included multiplying a patient's dead space normalized carbox ratio by the mean dead space value calculated over the entire population of evaluated patients. This application of the mean values created a comparison of the normalized carbox value with the non-normalized carbox value. Applying this constant term, the mean value of a normalization factor, to calculated normalized carbox ratios produces no affect on the calculated sensitivity and specificity directly, but instead affects thresholds for data analysis performed by the system 10.

3. Normalizer Effectiveness Measurement

The study next included evaluating each normalization factor's effectiveness using graphical methods. The normalized carbox values and the original carbox value for the patient population comprised a receiver operator curve. A threshold for separating patients with pulmonary embolism and patients without pulmonary embolism was chosen. This threshold value drove a determination from the data of how many patients were correctly identified as having pulmonary embolism, i.e. the sensitivity, and how many patients were correctly identified as having no pulmonary embolism, i.e. the specificity. By varying the threshold, a plot of sensitivity versus (1-specificity) was generated. This curve was the receiver operator curve.

The primary metric for evaluating each normalization factor was the specificity when 95% of pulmonary embolisms were properly diagnosed, i.e., the Spec95 or the specificity when the threshold was set so that the sensitivity was 95%. All of the normalization factors described above have the characteristic that the Spec95 is larger for the normalized data than for the original, non-normalized carbox value.

FIGS. 17 through 27 represent normalization factor data for this exemplary study using the Spec95 metric.

The present invention has been described herein with reference to its preferred embodiments, including several illustrative variations thereof. However, it should be understood that those skilled in the art readily could devise many obvious and trivial modifications of those preferred embodiments that nevertheless do not depart from the scope of the present invention, which is set forth in the following claims.

We claim:

1. A method for identifying pulmonary embolism in patients, the method comprising the steps of:
   a) measuring a D-dimer concentration in a blood sample;
   b) determining whether the measured D-dimer concentration is between 100 and 2000 nanograms per milliliter;
   c) performing, a respiratory test comprising the steps of:
      i) measuring a concentration of produced carbon dioxide in a volume of exhaled air;
      ii) measuring a concentration of unconsumed oxygen in the volume of exhaled air;
      iii) calculating a carbox ratio wherein the carbox ratio represents the concentration of produced carbon dioxide in relation to the concentration of unconsumed oxygen;
      iv) determining whether the calculated carbox ratio is less than or equal to a carbox ratio threshold in a range of 0.25 and 0.30; and
   d) outputting an indication, in cases when the measured D-dimer concentration is between 100 and 2000 nanograms per milliliter and the calculated carbox ratio is less than or equal to the carbox ratio threshold in the range of 0.25 and 0.30, that a pulmonary embolism is likely; or
   e) outputting an indication, in cases when the measured D-dimer concentration is between 100 and 2000 nanograms per milliliter and the calculated carbox ratio is greater than the carbox ratio threshold in the range of 0.25 and 0.30, that additional diagnostic testing is required; or
   f) outputting an indication, in cases when the D-dimer concentration is not between 100 and 2000 nanograms per milliliter and the calculated carbox ratio is greater than the carbox ratio threshold in the range of 0.25 and 0.30, that a pulmonary embolism is unlikely.

2. The method of claim 1, wherein the threshold indicative of concern is between 500 and 1000 nanograms per milliliter.

3. The method of claim 1 wherein the threshold indicative of concern is 500 nanograms per milliliter.

4. The method of claim 1, wherein the carbox ratio threshold is 0.28.

5. The method of claim 1 further comprising the step of heating the volume of exhaled air to prevent condensation from forming.

6. The method of claim 1 wherein the threshold indicative of concern is about 500 nanograms per milliliter and the carbox ratio threshold is about 0.28.

7. A method for identifying pulmonary embolism in patients, the method comprising the steps of:
   a) determining whether a concentration of D-dimer in a blood sample is at 100 and 2000 nanograms per milliliter;
   b) determining whether a carbox ratio of a volume of exhaled air is in the range of 0.25 and 0.30; and
   c) outputting an indication, in cases when the measured D-dimer concentration is between 100 and 2000 nanograms per milliliter and the calculated carbox ratio is less than or equal to the carbox ratio threshold in the range of 0.25 and 0.30, that a pulmonary embolism is likely; or
   d) outputting an indication, in cases when the measured D-dimer concentration is between 100 and 2000 nanograms per milliliter and the calculated carbox ratio is greater than the carbox ratio threshold in the range of 0.25 and 0.30, that additional diagnostic testing is required; or
   e) outputting an indication, in cases when the D-dimer concentration is not between 100 and 2000 nanograms per milliliter and the calculated carbox ratio is greater than the carbox ratio threshold in the range of 0.25 and 0.30, that a pulmonary embolism is unlikely.

8. The method of claim 7, wherein the threshold indicative of concern is between 500 and 1000 nanograms per milliliter.

9. The method of claim 7 wherein the threshold indicative of concern is 500 nanograms per milliliter.

10. The method of claim 7, wherein the carbox ratio threshold is 0.28.

11. The method of claim 7 further comprising the step of heating the volume of exhaled air to prevent condensation from forming.

12. The method of claim 7 wherein the threshold indicative of concern is about 500 nanograms per milliliter and the carbox ratio threshold is about 0.28.

* * * * *